United States Patent [19]
Johnson

[11] Patent Number: 5,658,328
[45] Date of Patent: Aug. 19, 1997

[54] ENDOSCOPIC ASSISTED MASTOPEXY

[76] Inventor: Gerald W. Johnson, 16000 Steubner Airline #105, Spring (Houston), Tex. 77379

[21] Appl. No.: 419,382

[22] Filed: Mar. 30, 1995

[51] Int. Cl.$^6$ .................................................... A61F 2/12
[52] U.S. Cl. .............................................. 623/8; 128/898
[58] Field of Search ........................... 623/7, 8; 128/898

[56] References Cited

U.S. PATENT DOCUMENTS

| | | | |
|---|---|---|---|
| 5,039,198 | 8/1991 | VanBeek | 385/117 |
| 5,500,019 | 3/1996 | Johnson et al. | 623/8 |

OTHER PUBLICATIONS

M.A.F. Correa, MD., "Videoendoscopic Subcutaneous techniques for aesthetic and reconstructive plastic surgery", *Plastic and Reconstructive Surgery*, pp. 446–453, Aug. 1995.

*Primary Examiner*—Randy C. Shay
*Attorney, Agent, or Firm*—Neal J. Mosely

[57] ABSTRACT

An endoscopic assisted mastopexy, with or without augmentation, or an endoscopic assisted reduction mammoplasty is disclosed in which an incision is made at a point on the body remote from the breast which is not ordinarily visible, such as in a preexisting scar, under an armpit or elsewhere accessible to the upper hemisphere of the breast. In the mastopexy with augmentation, dissection is carried up to the fascia of the pectoralis muscle and above the fascia and with the scope for visualization, an endotube is inserted from the incision over the pectoral fascia. A tissue expander is inserted and inflated to dissect the fascia away from the muscle to form a posterior pocket and then removed. With blind dissection, with external palpation, using scissors, from the incision, the skin is undermined in the upper quadrant. The pocket is then connected from the subcutaneous position and the breast tissue is released by cutting loose to yield a direct communication from the subcutaneous pocket around to the postglandular pocket. The soft tissue of the breast is elevated away from the pectoralis muscle and fascia going up above the second rib and just below the clavicle to lift and position the nipple areolar complex. The upper pole of the breast is sutured into the prepectoral fascia. An implant is placed into the pocket and then inflated with saline as in an endoscopic augmentation. The initial incision is closed and the patient is dressed and provided with support during recuperation and healing. Nipple reduction, if necessary, is accomplished by undermining the areolar border and placing a permanent circum-aroelar suture through stab wounds which allows a reduction in nipple size by the purse-string suture without any scars around the nipple. In the mastopexy without augmentation, the implant is omitted. In the reduction mammoplasty, breast tissue is removed and the breast repositioned and reshaped.

24 Claims, 24 Drawing Sheets

ENDOSCOPIC ASSISTED MASTOPEXY

BACKGROUND OF THE INVENTION

1. Field of the Invention

This invention relates to new and useful improvements in breast surgery and more particularly to an endoscopic assisted mastopexy (breast elevation), including reduction mammoplasty (surgical removal of breast tissue) and mastopexy with prosthetic augmentation. The invention relates generally to a surgical procedure utilizing an endotube, obturator and/or other appropriate instruments, utilizing at least one small hidden incision, under the armpit, or in a preexisting scar, or other substantially unobservable locations.

2. Brief Description of the Prior Art and History of Breast Reduction Surgery Mastopexy (surgical elevation of the breast and reduction mammoplasty (surgical removal of breast tissue) has been known and successfully carried out for many years.

The surgeon's quest for the ideal method of breast reduction began long before there was a specialty of plastic surgery. Many names associated with the reduction mammoplasties in the 1920's included Thorak, Morestin, Joseph, Dufourmentel, and de Quervain.

Dr. Biesenberger, in *Biesenberger, H., Deformitaten and kosmetische operationen der weiblichen Brust*. Vienna: Maudrich, 1931, described an extensive glandular resection with nipple transposition in which he did a very wide undermining of the skin with exposure of the gland. Certain variations of his technique are still used today with some plastic surgeons who agree fully with wide undermining and others who do not agree with wide undermining.

The gynecologists and general surgeons for many years learned and practiced their skills by making large incisions and under direct vision healing their patients. General surgery residents were taught that a skin incision heals from side to side, not end to end, therefore making all incisions as long as necessary. The reason for discussing and showing the techniques of doing the "open" circumareolar reduction mammoplasties, mastopexies, and mastopexies with augmentation, is because when surgery is done through the axilla, exactly the same work is done inside as has been done in the "open" circumareolar technique save for two factors.

Dr. Robert J. Wise, (Wise, R., A Preliminary Report of a Method of Planning the Mammoplasty. Plast. Reconstr. Surg. 17:367, 1956), working in Houston, Tex., had analyzed and come up with some of the earliest ideas, methods, and techniques to accomplish a reduction mammoplasty and obtain symmetrical results with excellent preservation of the nipple and skin and with free grafting of the nipple in large breasts.

Dr. J. Strombeck (Strombeck, J., Mammoplasty: Report of a new technique based on the two-pedicle procedure. Br. J. Plast. Surg. 13:79, 1960) reported on his new technique for breast reduction based on the two pedicle procedure.

Dr. T. Skoog (Skoog, T., A technique of breast reduction. Transposition of the nipple on a cutaneous vascular pedicle. Acta Chir. Scand, 126:453, 1963) reported on his new technique of breast reduction by transposition of the nipple on a continuous vascular pedicle and by 1967, Dr. I. Pitanguy (Pitanguy, L., Surgical treatment of breast hypertrophy. Br. J. Plast. Surg. 10: 78, 1967 ) reported on his technique of treatment of breast hypertrophy in an effort to give a better shape and better results postoperative.

Up to this point in the late 1960s the two primary considerations in doing the reduction mammoplasties were (1) do not have any necrosis of the skin or the nipple and (2) get an adequate reduction with as good a form as possible. No real consideration was being given to sensation in the nipple nor the ability of the nipple to lactate and function to nurse an infant should that become necessary.

Beginning in about 1973 Dr. L. Ribeiro (Ribeiro, L. A new technique for reduction Mammoplasty. Plast. Reconstr. Surg. 55:330, 1975) began doing reduction mammoplasties using an inferiorly based pedicle flap. He reported his work in March of 1975 and this was the first report of a new procedure that had a tremendous influence on the type of reductions that are done presently. Dr. Ribeiro's inferiorly based pedicle flap to preserve the nipple was also one of the first procedures designed in reduction mammoplasty that gave an excellent chance for preservation of sensation of the branches of both medial and lateral sensory nerves to the nipple as well as the possibility of lactation.

Then Dr. T. Robbin (Robbins, T. Reduction Mammoplasty with the Areolar-Nipple Based on an Inferior Pedicle. Plast. Reconstr. Surg. 59: 64, 1977) reported in 1977 of his experiences with a reduction mammoplasty with the areolar-nipple complex based on an inferior dermal pedicle. Dr. Robbins was especially aware that his technique meant that nipple sensation was more often retained than other methods of reduction.

The efforts of Dr. Ribeiro and Dr. Robbins in promoting the inferior pedicle technique was given a tremendous boost when in April of 1977, Dr. Courtiss and Dr. Goldwyn (Courtiss, E. and Goldwyn, R. Reduction mammoplasty by the inferior pedicle technique. Plast. Reconstr. Surg. 59: 500, 1977) published their article on reduction mammoplasty by the inferior pedicle technique. Dr. Courtiss and Goldwyn likewise found that the resulting breast sensation in their series of patients was better than obtained after other methods of reduction mammoplasty. They likewise found that the inferior pedicle technique was a versatile method for reduction for both large and small breasts and they found that any result that you could obtain by another method you could basically obtain with the inferior pedicle technique and complications were certainly no more, and probably less, than any other technique. They felt that with regard to the resulting nipple and areolar sensation that the inferior pedicle technique had the benefit of preserving the important cutaneous branches of the fourth, fifth, and frequently the third intercostal nerves. They stated that patients with normal sensations before surgery usually showed no change after the operation.

By the beginning of the 1980s, of the five primary goals of the patient and surgeon for breast reduction, the average plastic surgeon was now able to achieve either fully or partially four of these goals.

1. A breast of ideal size for the patient elevated to a normal position.

2. A breast of ideal form or shape for the patient.

3. A breast with normal sensation and erectile function of the nipple.

4. A breast that could lactate and could function normally in nursing.

Goldwyn's objectives modified by Haubin, see Finger, R. et al. Superiomedial Pedicle Technique of Reduction Mammoplasty. Discussion. Plast. Reconstr. Surg. 83: 471, 1989, for the optimal reduction mammoplasty are: safe, simple, speedy, sensation preserved, symmetry, suitably shaped and sexy breasts, and sine sanguine (bloodless) operation.

However, there still remained the problem of scarring and no one was yet able to eliminate the excessive scarring involved, especially with large reductions.

In the 1980s, the plastic surgeons began to turn their attention to reaching the further goal of the patient and surgeon, a breast with a minimal amount of scarring or minimal amount of visible scarring. Too many plastic surgeons for too many years have accepted scarring as an inevitable part of our profession. Elimination of scars is a most desirable goal to be reached.

Dr. S. Hoffman (Hoffman, S. Discussion. Elimination of the vertical scar in reduction mammoplasty. Plast. Reconstr. Surg. 89: 468, 1992) commented that it is hard to believe we are still inventing new procedures for breast reductions and he did accurately observe that many of the techniques are not really new and one would be amazed at how often a careful review of the older literature yields surprisingly new information.

With the dawn of increased interest in the elimination of the scars, or at least minimizing of the scars and making them less visible, Dr. G. Peixoto (Peixoto, G. Reduction mammoplasty: A personal technique. Plast. Reconstr. Surg 65: 217, 1980) reported a personal technique of his in the methods to reduce scarring.

Drs. C. Marachac and G. De Olarate (Marshac, C., and De Olarte, G. Reduction mammoplasty and correction of ptosis with a short inframammary scar. Plast. Reconstr. Surg. 69: 45, 1982) reported reduction mammoplasty and correction of ptosis with a short inframammary scar in 1982.

In 1986, Dr. E. DeLongis (DeLongis, E., Mammoplasty with an L-shaped limited scar and retropectoral dermopexy. Aesthetic Plast. Surg. 10: 171, 1986) reported a mammoplasty with an L-shaped limited scar and retropectoral dermopexy.

Dr. F. Marconi (Marconi, F. The dermal purse-string suture: A new technique for a short inframammary scar in reduction mammoplasty and dermal mastopexy. Ann. Plast. Surg. 22: 484, 1989) reported the use of a dermal purse-string suture and a new technique for short inframammary scar in reduction mammoplasty and dermomastopexy.

Dr. L. Benelli, in 1990, (Benelli, L. A new periareolar mammoplasty: The "Round Block" technique. Aesthetic Plast. Surg. 14: 93, 1990) reported a new technique for periareolar mammoplasty by what he described as the "round block" technique. Dr. Benelli has also continued to be very active in this field of reduced scarring and has been promoting this very actively.

Johnson U.S. Pat. No. 5,258,026 discloses a surgical procedure for breast augmentation in which an incision is made inside the navel or umbilicus. An endotube which has an obturator with a bullet shaped tip is introduced into this incision and pushed from the umbilicus, staying just above the fascia of the interior abdominal and chest wall, and below the subcutaneous tissue and fat, to a position behind the breast. The obturator is removed and an endoscope used to verify the proper location of the tunnel. The endotube is removed leaving a temporary tunnel leading to a space behind the breast. A hollow prosthesis is rolled up tightly, positioned inside the end of the endotube and pushed into the tunnel behind the beast. The prosthesis is held in place by the hand of the surgeon on the breast and the endotube removed. The prosthesis is pumped full of saline solution to about a 50% over-fill. The filling of the prosthesis with saline solution, together with the manipulation and pressure by the surgeon causes the tissues behind the breast to be dissected to form a pocket filled by the implant. After a short time, excess liquid is allowed to flow out of the prosthesis and the fill tube removed. The procedure is then repeated for the other breast. The navel is sutured and the patient may then go home from the recovery room.

SUMMARY OF THE INVENTION

One of the objects of this invention is to provide a new and improved surgical procedure comprising an endoscopic assisted mastopexy.

Another object of this invention is to provide a new and improved procedure for breast surgery comprising an endoscopic assisted reduction mammoplasty.

Another object of this invention is to provide a new and improved procedure for breast surgery comprising an endoscopic assisted reduction mastopexy with breast augmentation.

Another object of this invention is to provide a new and improved procedure for breast surgery comprising an endoscopic assisted mastopexy which utilizes at least one small hidden incision, under the armpit, or in a preexisting scar, or other substantially unobservable location but accessible to the upper hemisphere of the breast.

Another object of this invention is to provide a new and improved procedure for breast surgery comprising an endoscopic assisted mastiopexy in which there is minimal bleeding, bruising and swelling.

Another object of this invention is to provide a new and improved procedure for breast surgery comprising an endoscopic assisted mastopexy in which there is much less damage to nerves than caused by other techniques currently used.

Another object of this invention is to provide a new and improved surgical procedure comprising an endoscopic assisted mastopexy which reduces postoperative pain and virtually eliminates visible scarring.

Another object of this invention is to provide a new and improved surgical procedure comprising an endoscopic assisted mastopexy which permits the direct, undistorted visualization of the site during the operation.

Another object of this invention is to provide a new and improved procedure for breast surgery comprising an endoscopic assisted mastopexy which utilizes at least one small hidden incision, under the armpit, or in a preexisting scar, or other substantially unobservable location through which a pocket is opened behind the upper hemisphere of the breast, and the breast elevated and the upper portion secured to the prepectoral fascia.

Another object of this invention is to provide a new and improved procedure for breast surgery comprising an endoscopic assisted mastopexy which utilizes at least one small hidden incision, under the armpit, or in a preexisting scar, or other substantially unobservable location through which a pocket is opened behind the upper hemisphere of the breast, the breast elevated and the upper portion secured to the prepectoral fascia, and an implant is rolled up and placed into the pocket behind the breast and then inflated again with saline.

Another object of this invention is to provide a new and improved procedure for breast surgery comprising an endoscopic assisted mastopexy which utilizes at least one small hidden incision, under the armpit, or in a preexisting scar, or other substantially unobservable location through which a pocket is opened behind the upper hemisphere of the breast, the breast elevated and the upper portion secured to the prepectoral fascia, and breast tissue is removed and the breast repositioned and reshaped.

Other objects of the invention will become apparent from time to time throughout the specification and claims as hereinafter related.

The techniques that will be described below for this method of reduction mammoplasty combines parts of several procedures or techniques that are already recorded in the literature. However, there has been no reported combination of the techniques in the manner described below to attain the reduction mammoplasty, the mastopexy, and the mastopexy with augmentation. Also the necessary adjunctive use of the endoscope with this combination of other techniques allows introduction of these procedures as truly new and innovative.

BRIEF DESCRIPTION OF THE DRAWINGS

FIGS. 2a and 2b show a breast in section and in elevation, respectively, in a mastopexy. FIGS. 2e and 2f show a breast in section and in elevation, respectively, in a mastopexy with augmentation.

DEVELOPMENT OF THE INVENTION

Figure 1:
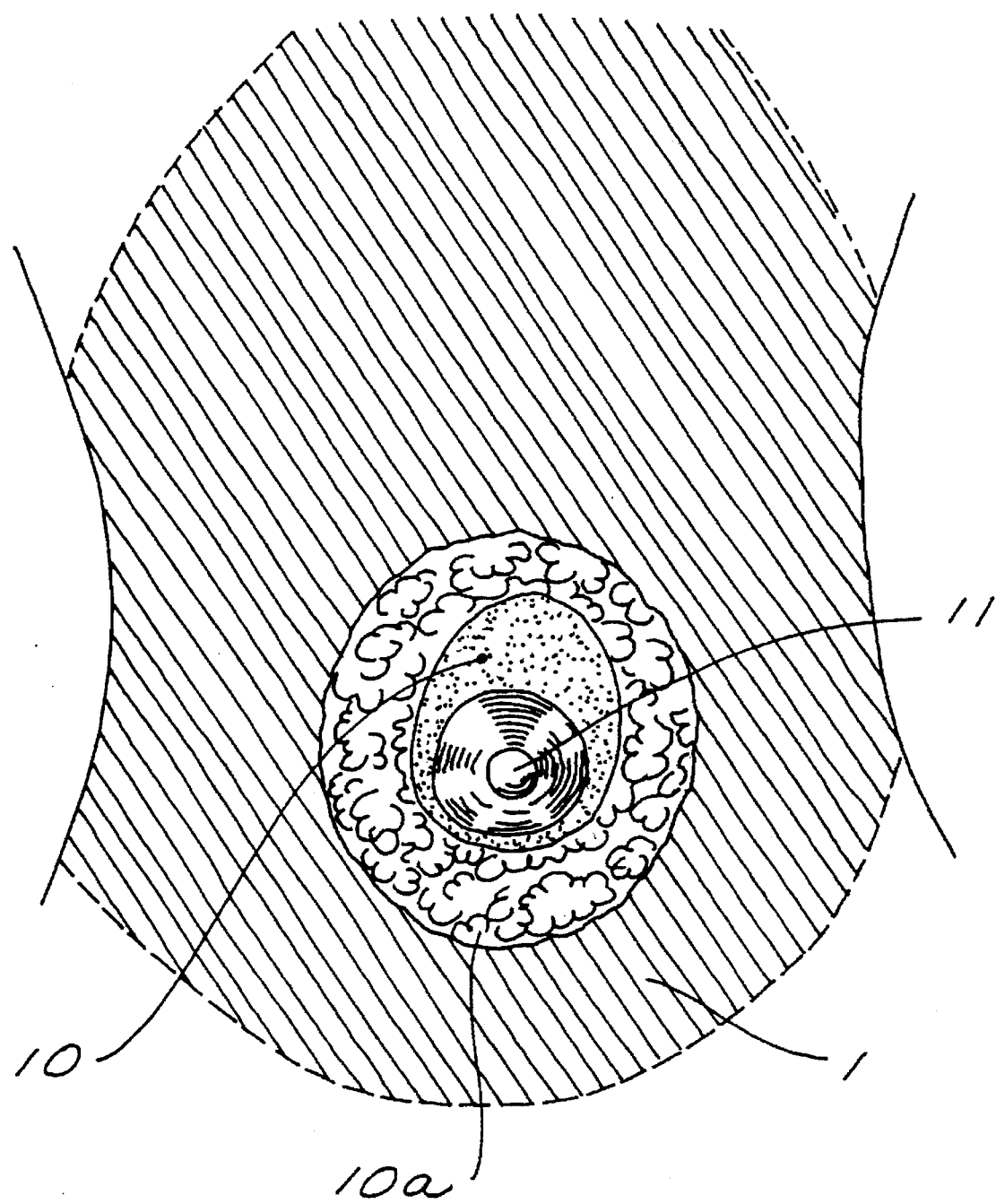
FIG. 1 is a view, partly in section, illustrating the circumareolar reduction mammoplasty or mastopexy in which the incision was made around the nipple.

The gynecologists and general surgeons for many years learned and practiced their skills by making large incisions and under direct vision healing their patients. General surgery residents are taught that a skin incision heals from side to side, not end to end, therefore making all incisions as long as necessary. Many years before plastic surgeons knew the word "endoscopically", other surgeons had already started doing it. They were doing the very same surgery internally and still healing their patients, but with a much smaller skin incision.

The reason for discussing and showing the techniques of doing the "open" circumareolar reduction mammoplasties, mastopexies, and mastopexies with augmentation, is because this surgery done through the axilla, is the same as is done in the "open" circumareolar technique save for two factors. First, there is no incision made around the nipple; and second, endoscopic assistance can be used to visualize where the surgeon is going in order to elevate, project and suture the breast properly.

Aesthetics are a major factor in breast surgery. According to Gombrich, (Gombrich, E., The Source of Order: Pharidon Press, 1979. P. 54.), Owen Jones stated a century ago that the most beautiful proportions are those which are the most difficult for the eye to detect. Birkhoff (Birkhoff, G. Aesthetic Measure. Cambridge, Mass.: Harvard University Press, 1933 P. 4.) defined the aesthetic value of any object as the ratio between order and complexity: pleasure of perception derives from a high degree of order, harmony, balance, unity, and contrast when combined with a lower degree of confusion and complexity. In plastic surgery, it is the surgeon's job to paint the Mona Lisa, and unlike Leonardo, he cannot throw the canvas away and start over if he made a mistake or produces a bad result. Therefore, it is obvious why so many excellent surgeons develop their own techniques in the ongoing effort to paint the perfect reduction mammoplasty.

The first thing that should be evaluated is the primary goal of the patient and the surgeon in doing a breast reduction, mastopexy, or mastopexy with augmentation.

1. A breast of ideal size for the patient elevated to a normal position on the chest wall.

2. A breast of ideal form or ideal shape for the patient.

3. A breast with a minimal amount of scarring or visible scarring.

4. A breast with normal sensation and erectile function of the nipple.

5. A breast that can lactate and can function normally for nursing, if necessary.

Those patients in whom the goal of good cosmetic results take primary consideration, or at least equal consideration with the health or comfort of the patient, are the subjects of this invention.

Any new technique in any branch of surgery must be one that can be learned by the average surgeon who can then operate on his patient and produce the average results the new procedure is designed to produce. Any technique that is so complicated or requires a more skillful surgeon or the most complicated and expensive instruments to reproduce comparable results is a technique that is not really useful in medicine or surgery to the majority of the people. As stated by Dr. Paul McKissock (McKissock, P., Breast Reduction Utilizing the Maximally Vascularized Central Breast Pedicle. Discussion. Plast. Reconstr. Surg. 76:899, 1985.), "No matter how appealing or doubtful a new operation may seem in print, its true value ultimately must be measured by its reproducibility in the hands of others."

This inventor, (Johnson, G. Central core reduction mammoplasties and Marlex suspension of breast tissue. Aesthetic Plast. Surg. 5: 77, 1981), having trained under Dr. Robert J. Wise at the University of Texas Hermann Hospital in Houston, Tex., had a good working knowledge of the mechanics of reduction mammoplasty, as well as the planning of reduction mammoplasties upon entering private practice. His interest, however, in the primary goals of patient and surgeon soon led to areas beyond what had been learned working with Dr. Wise. Frequently procedures did not account for the nerve supply and obviously when there was a need for a large reduction with free grafting of the nipple, there would be sensory loss of the nipple.

Therefore, in the mid-1970s independent of the knowledge of the work of Dr. Robbins, Dr. Ribeiro, Dr. Courtiss, and Dr. Goldwyn, this inventor, Dr. G. W. Johnson, began a technique described as the central core reduction mammoplasty with the nipple based on an inferior pedicle which proved to be an excellent method of reduction. It gave good results and patients were able to enjoy the ideal size and normal position on the chest wall, the ideal form of the breast, they had the sensation in the nipple, and they could lactate for nursing should that become necessary.

In the mid-1980s we (the inventor and staff) began using the technique which we described as the cirumareolar reduction mammoplasty or mastopexy. This method incorporated the Biesenberger technique of extensive undermining and with exposure of the gland accomplishing whatever mechanical or structural changes that were needed internally. The incision 10 (FIG. 1) on the breast 1 was made around the nipple 11 and depending upon the size of the nipple, a basically concentric circle excision 10a was made around the nipple incision 10 to remove any excessive or undesired portion of areolar border with the upper portion of the concentric circle going slightly above the nipple which tended to give some elevation of the nipple. However, the minimal elevation of the nipple 11 gained from the concentric circle excision 10 was not the technique nor the method depended on to give the necessary elevation of the nipple.

Even in cases where there was not an excessive amount of areolar border, a concentric circle was designed around the incision 10 of the nipple 11 in order to give a larger circle which, when stretched out, gave a longer incision and therefore more exposure to the breast. We began using this technique in 1986 on patients who had very large breasts and needed reductions up to 1,000 to 1,500 grams per breast. We also used this procedure on patients who had ptotic breasts and needed the breast elevated with no implants added, and we did this procedure on patients who had ptotic breasts that needed to be elevated as well as having an implant put in place.

Initially, we encountered some problems and had a few complications that occurred because in our undermining of the skin away from the gland in the lower hemisphere we approached closer to the chest wall than the normal two centimeters that we try to leave at the present time. Maintaining the "2 centimeter distance" has previously been advocated by Hester et al. (Hester, T., Bostwick, J., Miller, L., and Cunningham, S. Breast reduction utilizing the maximally vascularized central breast pedicle. Plast. Reconstr. Surg. 76L 890, 1985).

When the upper hemisphere of the glands was then released from the muscle and detached from the periphery, the blood supply was coming in from the perforators and medial and lateral vessels from below. Occasionally, there was some compromise that resulted in superficial loss, and in one case full loss of a nipple on one patient. We soon realized, however, the necessity to pay attention to the method of dissection in the lower hemisphere of the breast and not approach closer than about two centimeters to the chest wall in the undermining of the skin away from the breast tissue.

We were confident from previous reports in the literature that the nipple could and would survive on just the glandular circulation by itself (Monfarreze, M., et al. Reduction mammoplasty by total dermoglandular pedicle. Aesthetic Plast. Surg. 9: 227, 1985. and Balch, C. The central mound technique for reduction mammoplasty. Plast. Reconstr. Surg. 67: 305, 1981.]). We also knew from the review of the anatomy and literature that when the medial and lateral blood supplies were protected, the nerve supply to the nipple was also much more likely to remain intact.

Initially, we will first be discussing in detail a form of circumareolar mastopexy. This is because for 8 years we have used the techniques and procedures on the gland via an areolar approach. These same techniques, tested and proven (and some were tested and discarded), are now being used through an axillary approach with endoscopic assistance which forms the present invention.

CIRCUMAREOLAR MASTOPEXY WITH AUGMENTATION

With the patient in preanesthesia in the erect position prior to induction of anesthesia, the marks are made on the chest with the nipple to fall in the mid-clavicular line about eighteen to twenty centimeters from the suprasternal notch, depending upon the height of the particular patient. This measurement, for location of the nipple, is more a perfunctory maneuver in this procedure because it is really not that critical to the surgical procedure itself.

Figure 3:
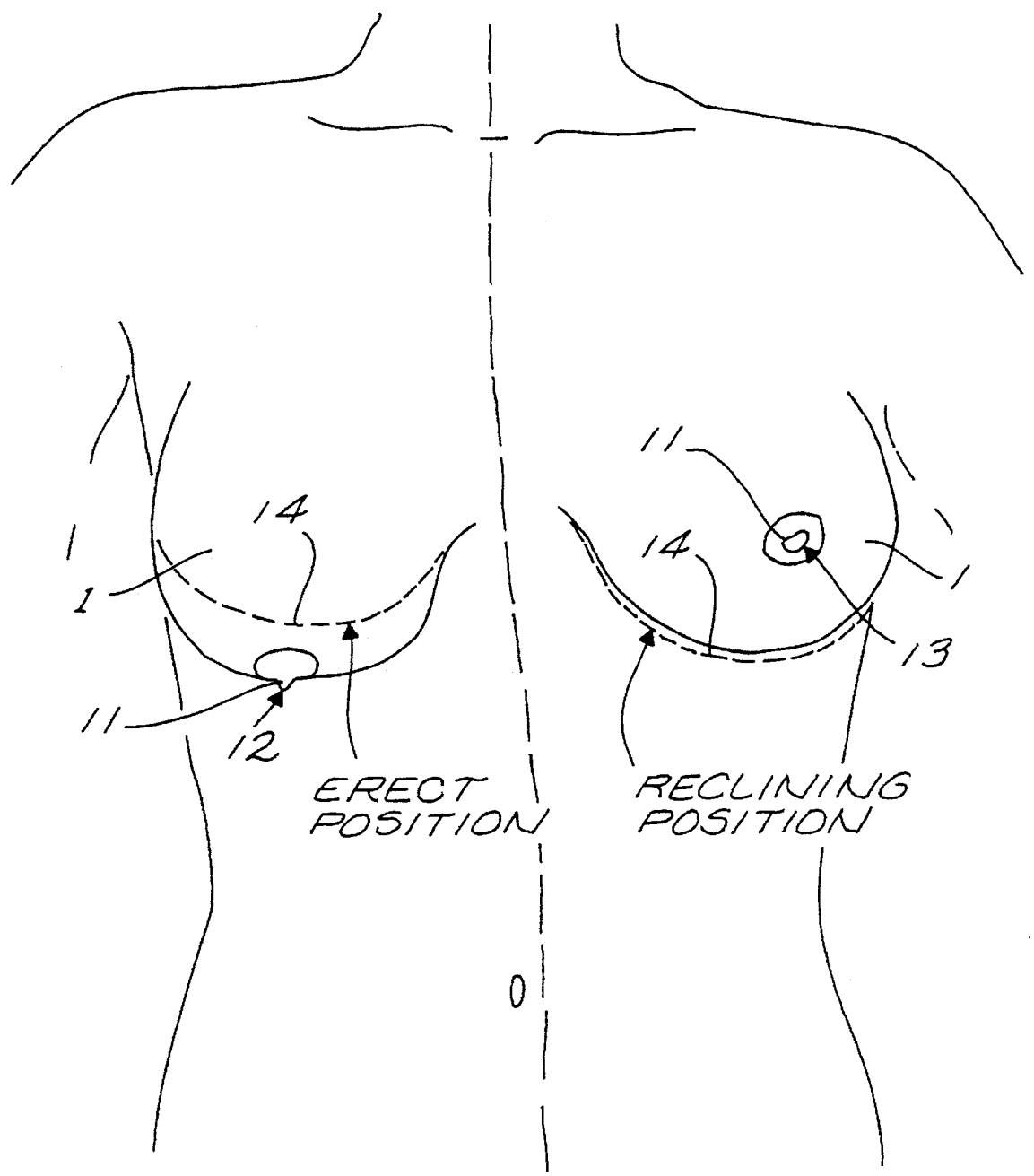
FIG. 3 shows the difference in positions of a woman's nipples on her chest wall in the erect position as compared to the reclining position.
Figure 4:
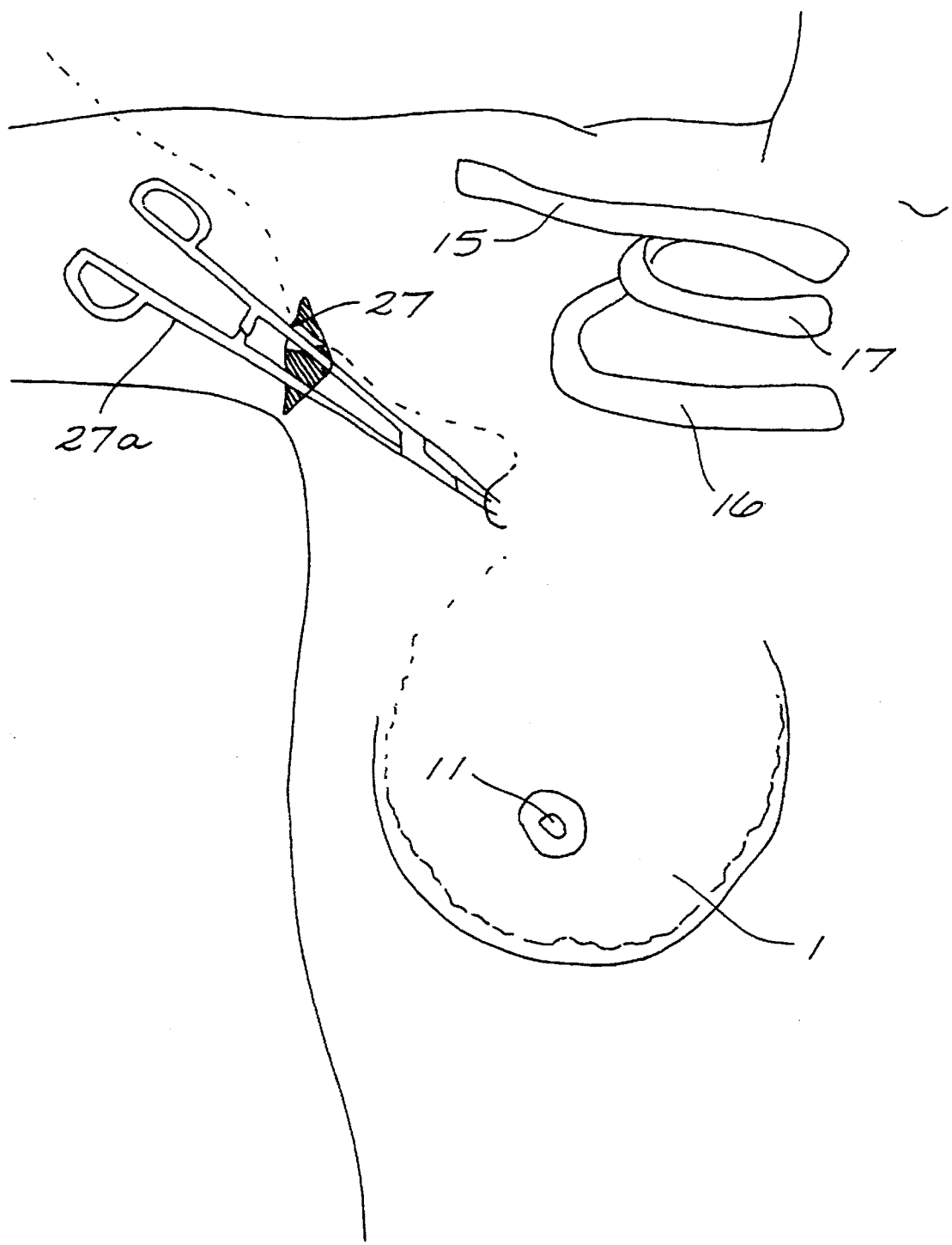
FIG. 4 shows fixed skeletal points such as the clavicle, second rib, and sternal angle in relation to the breasts for determining the position for entry of the surgical instruments.

Contrary to most reduction mammoplasty procedures where the preoperative marking of the nipple 11 and beast 1 are the most important step in the procedure, with this procedure preoperative marking actually is not necessary. The positions of a woman's nipples 11 on her chest wall are different in the erect 12 position versus the reclining position 13, see FIG. 3, in relation to the inframammary crease 14. However, fixed points on the skeleton do not change, thus our choice to use fixed skeletal points such as the clavicle 15, second rib 16, and sternal angle 17, see FIG. 4.

The patient is placed under general endotracheal anesthesia and prepped and draped in the routine manner for bilateral breast surgery. Antibiotics are given intravenously and then the breasts 1 are marked, at 2, for the appropriate location of the pocket that will contain the prosthesis later on. (FIG. 5) The incision 10 is designed around the nipple 11 and the concentric circle is made around the nipple marking and the concentric circle circumference is made only as large as necessary to gain access to the surgical site. The concentric circle technique is not in any way in this procedure used to help elevate the nipple as in the "doughnut" mastopexy.

Figure 2A:
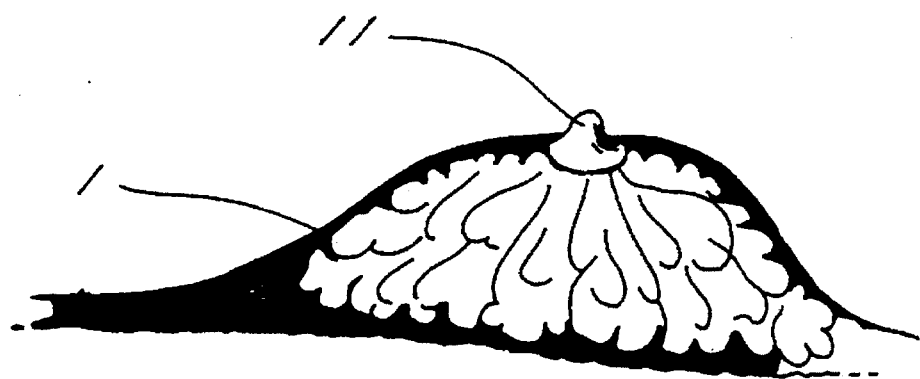
FIG. 2a and 2f illustrate the area of undermining and dissection in the mastopexy.
Figure 2B:
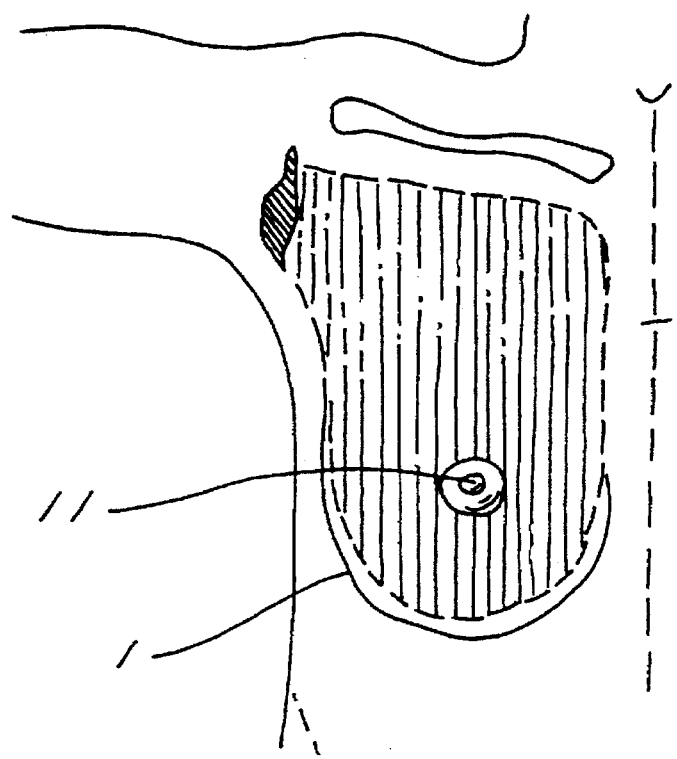
Figure 2C:
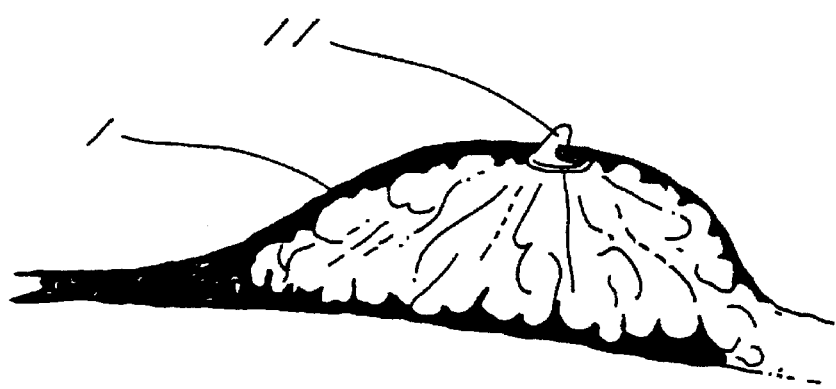
FIGS. 2c and 2d show a breast in section and in elevation, respectively, in a reduction mammoplasty.
Figure 2D:
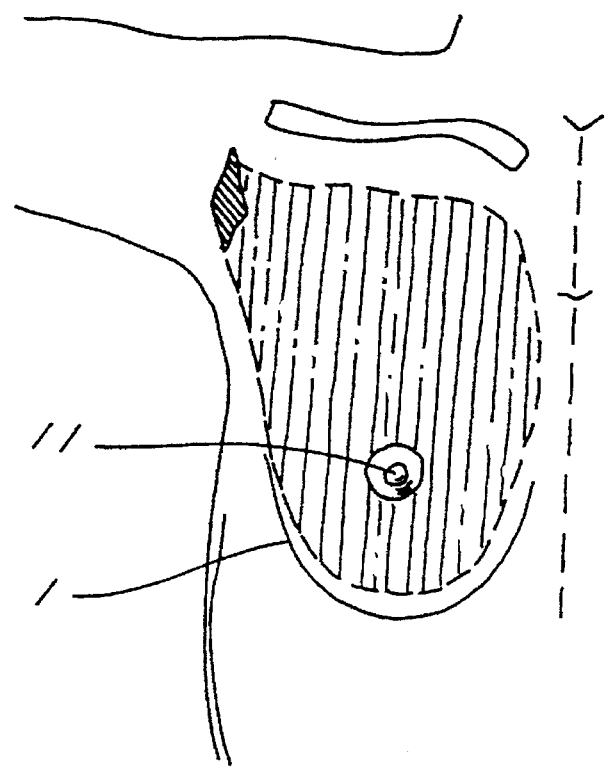
Figure 2E:
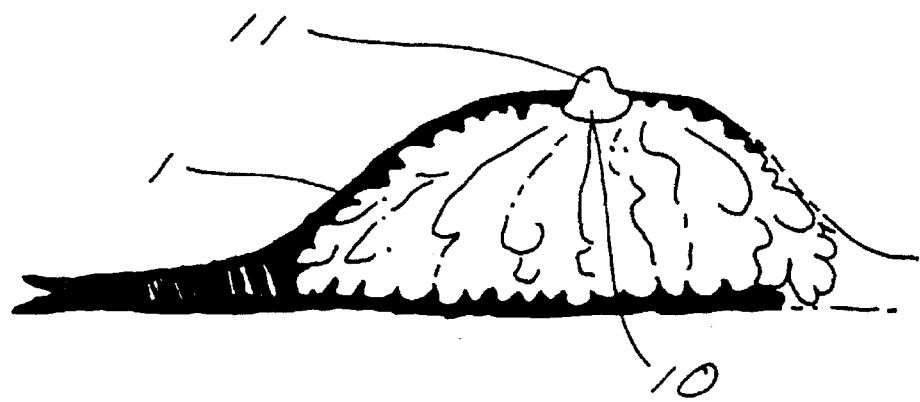
Figure 2F:
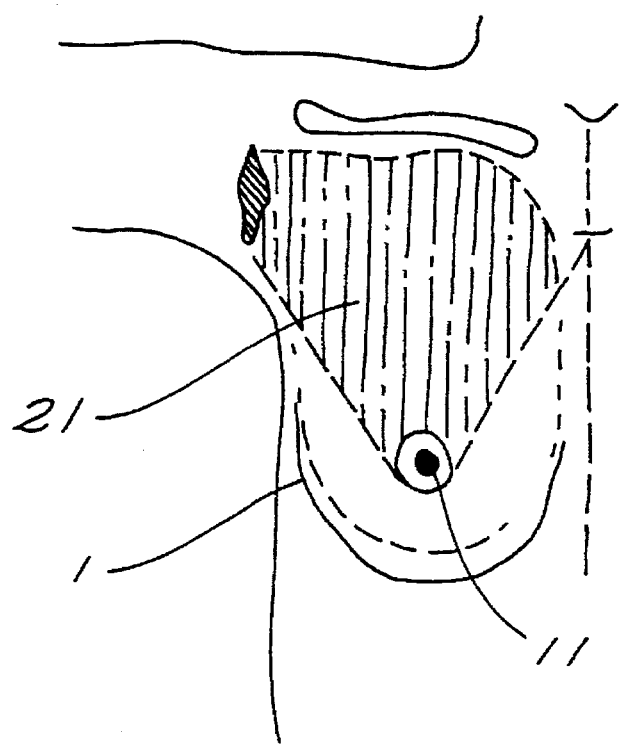
Figure 6:
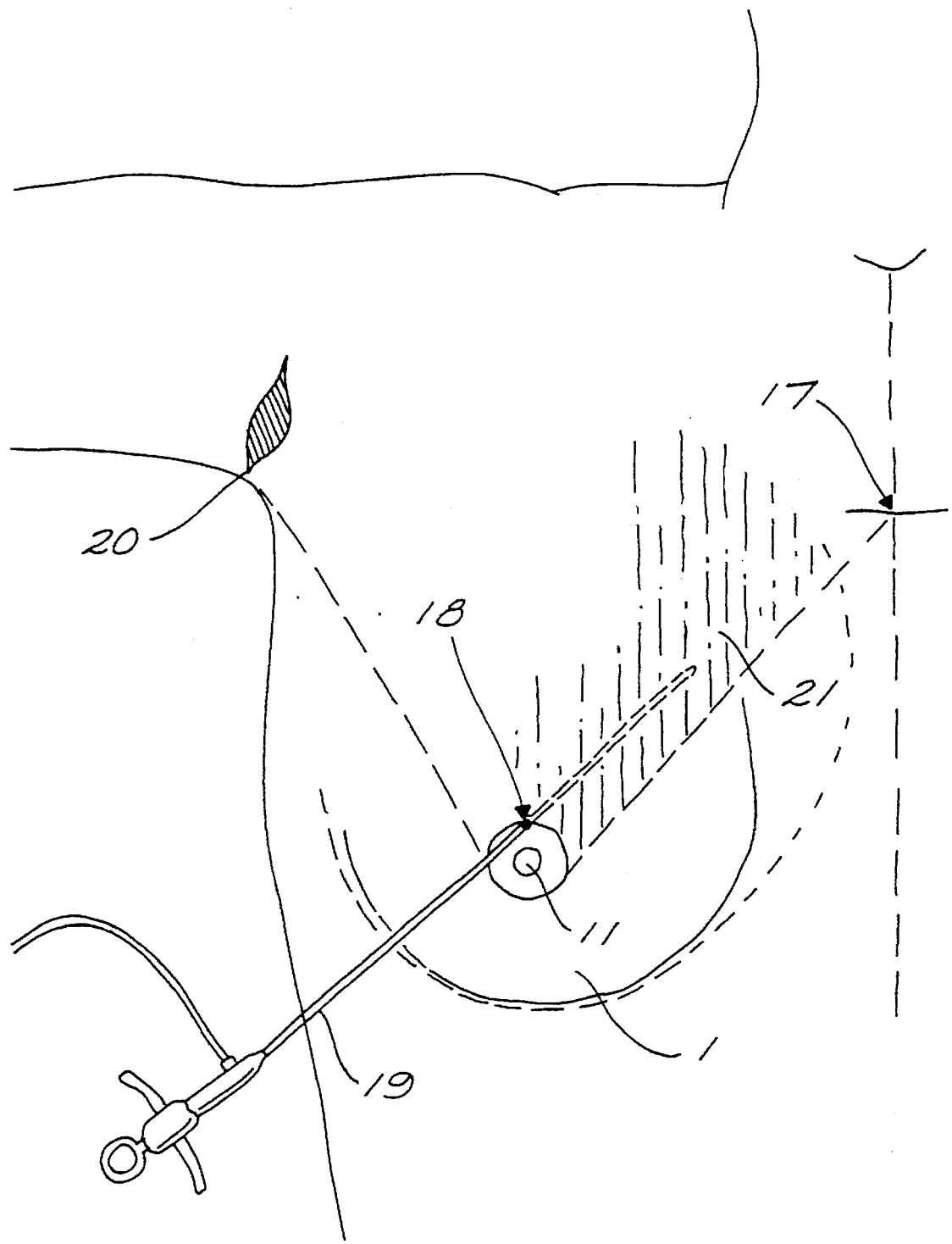
FIG. 6 shows the infiltration of the subcutaneous areas of the breast in an area from the nipple to the sternal angle and from the nipple to the mid-axillary area and up to the clavicle.

After these markings 2 have been made, a stab would 18 is made at the 6 o'clock position on the nipple (see FIG. 6). Then, using the long infiltration needle 19 that is used for the tumescent technique with liposuction, the subcutaneous areas of the breast are infiltrated in an area from the nipple 11 to the sternal angle 17 and from the nipple to the mid-axillary area 20 and up to the clavicle. This is the maximum amount of undermining done in the mastopexy with an augmentation (also see FIGS. 2e and 2f).

After this infiltration the incision is made and the skin is de-epithelized in the areas between the nipple markings and the concentric circle. After the skin has been de-epithelized, it is then cut through with the electrocautery. At this point, sharp dissection is done using scissors as if a subcutaneous mastectomy were being done, leaving a thin skin pedicle because of the ability of the skin to shrink and not fold upon itself is basically related to how much soft tissue is left attached to the skin. The dissection is carried out subcutaneously until the upper role of the breast is reached.

At a point which is not necessarily discreet (FIGS. 2e and 2f) but at which one can tell clinically that the upper margin of breast tissue ends and regular soft tissue beings, the dissection (shaded area 21) is carried from the subcutaneous plane through the soft tissue to the fascia of the pectoralis muscle. At this point the dissection is continued cephalad staying on top of the fascia of the muscle and from this point the dissection is done with the electrocautery, staying above the pectoral fascia and dissecting above the second rib up to about one centimeter below the clavicle. This is dissected along the arc that forms the classic cleavage and upper fullness of the female breast in the exaggerated pushed up position.

Figure 18:
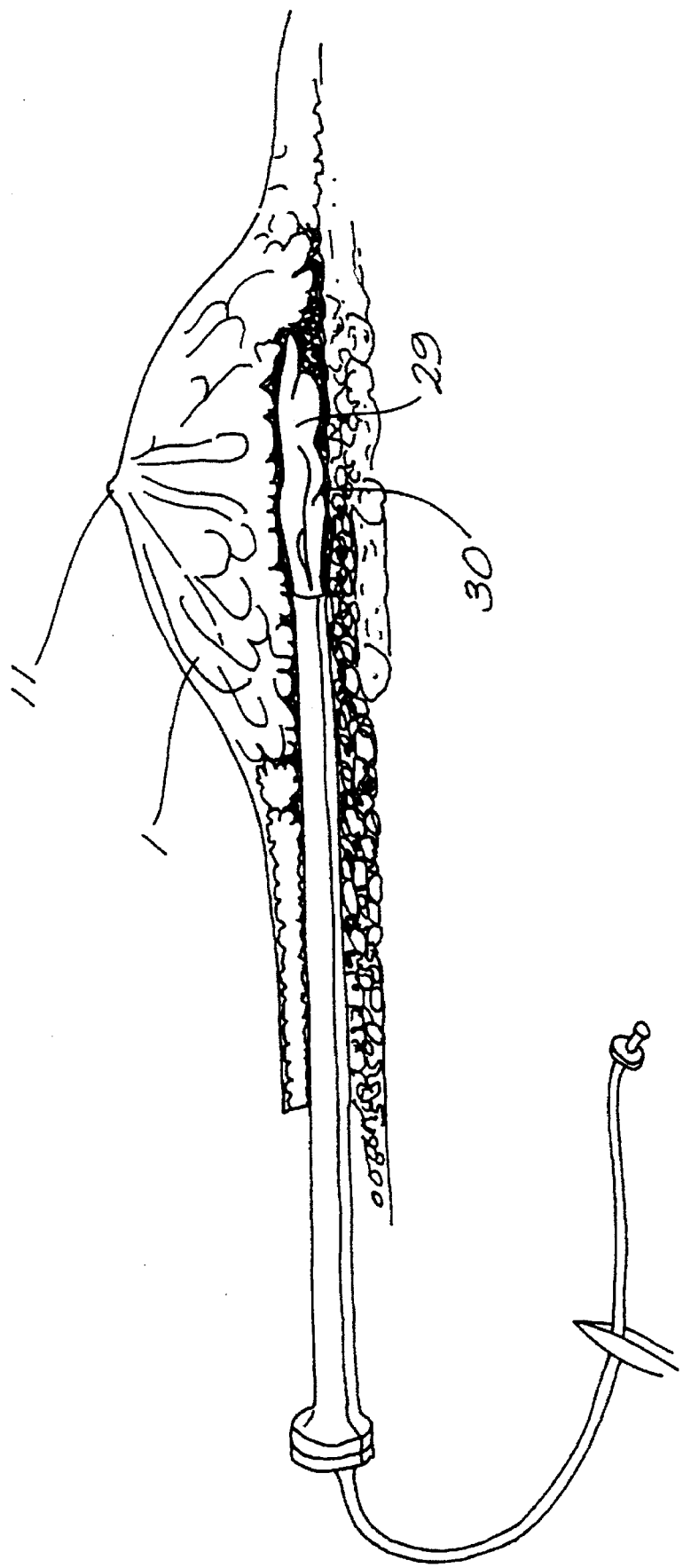
FIG. 18, in section, shows the insertion of a tissue expander which is inflated to form a pocket to receive an implant or prosthesis.

At this point the upper pole of the breast is lifted and, using the electrocautery, dissection is carried over the top of the breast tissue and dissected downward to make the retromammary pocket 21. The dissection of retromammary pocket 21 can be done using the expansion technique with a tissue expander and it is, in fact, the technique that is now used with the endoscopic axillary mastopexy (described for FIG. 18 below).

However, in the routine circumareolar mastopexy that we have done for the past nine years, we manually dissect under direct vision with the electrocautery the entire posterior pocket 21. At this point, the only place that the gland is detached from the skin is in the single quadrant formed by two lines from the nipple to the second rib and from the nipple to the axillary area (which form a 90° angle at the nipple), and bounded by the arc of the clavicle above.

Figure 7:
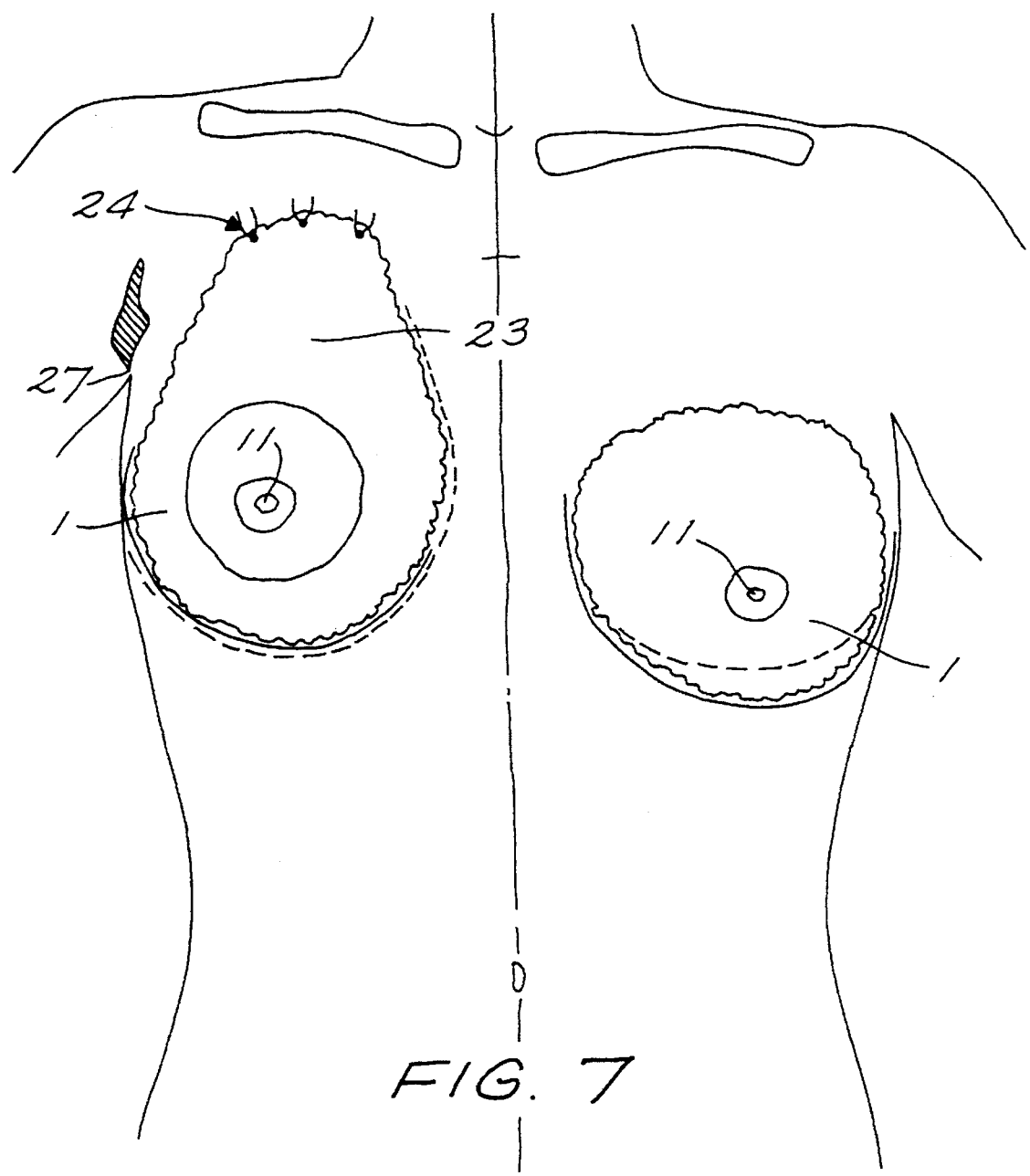
FIG. 7 shows the formation of the retromammary pocket for receiving a prosthesis in a mastopexy.
Figure 7A:
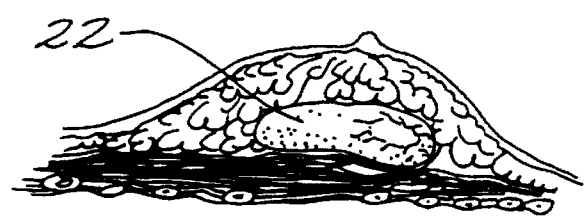
FIG. 7a is a section through the breast showing the retromammary pocket and a prosthesis in place.

After the pocket 21 has been made in the area that we have planned an appropriate pocket for the implant 22, the pocket 21 is then irrigated with antibiotic solution and the implant is slipped over the top of the breast and slipped down into the pocket. (FIG. 7) The pocket 21 is made larger by about fifty percent than the implant.

Figure 8A:
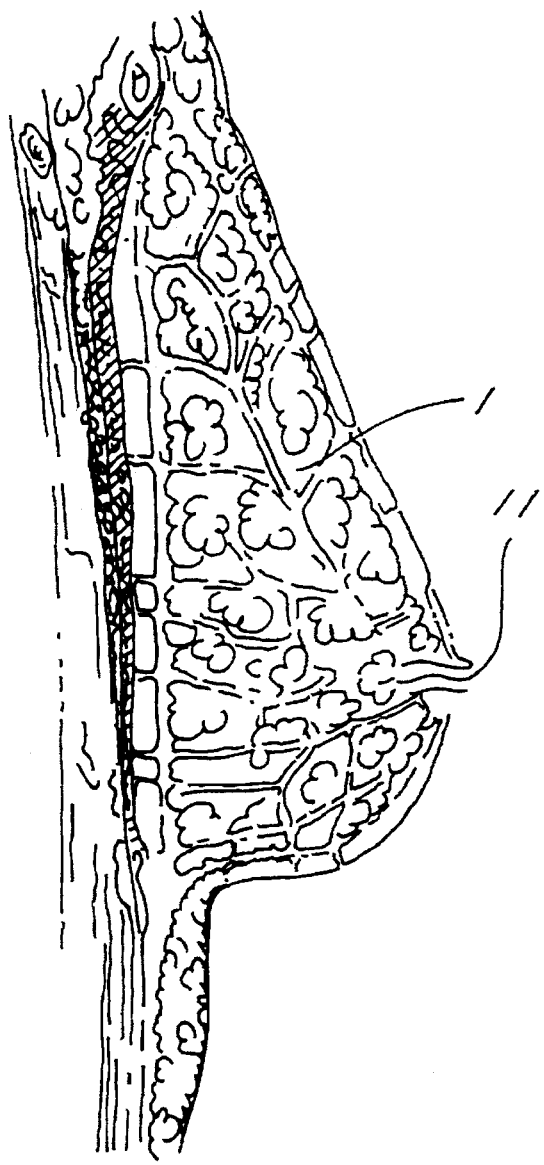
FIGS. 8 (before) and 8a (after) are sections through a breast showing the effects of aging on suspensory ligaments of Cooper stretching and lengthening which result in breast ptosis.
Figure 8:
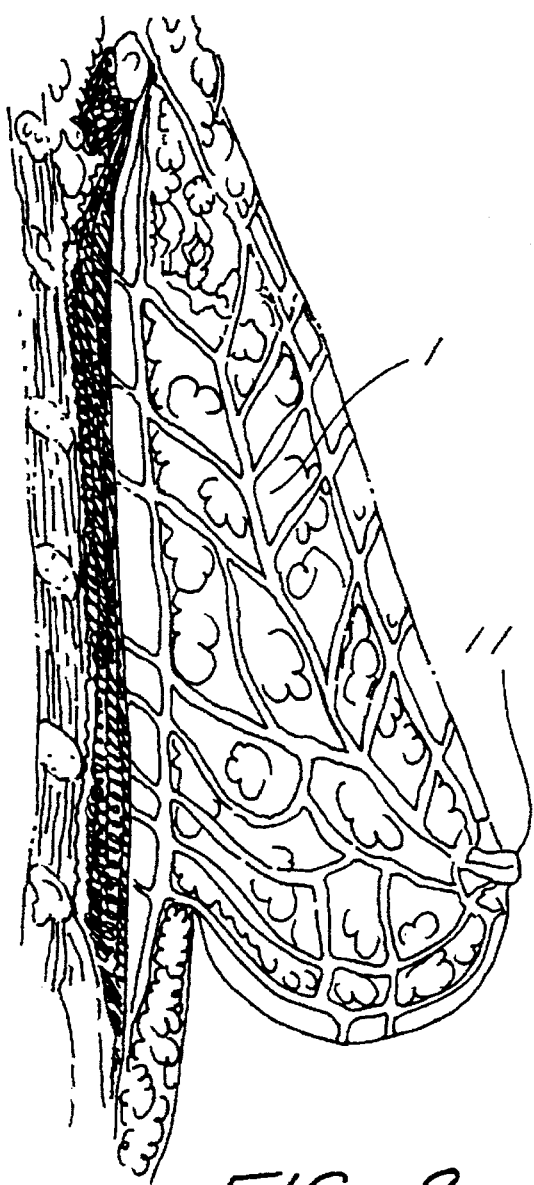

With the extra room in the pocket 21 the free upper quadrant 23 of the breast is pulled up and attached to the fascia in the area above the second rib, just below the clavicle starting from medially and going laterally it is attached with 20 Vicryl or Dexon sutures. Three to four sutures 24 along the upper arc of the breast to help recreate that arc, see FIG. 7. The upper margin of the breast is now back to the point which nature had it when the breast first developed. The breast is now elevated. Also, see FIG. 8 showing the breast 1 before surgery and FIG. 8a after surgery.

To correct for any discrepancies in preoperative positions of the nipples, make the distance from nipple to the upper margin of the breast the same on each side and suture that margin of the breast back into the fascia to elevate the nipple to the exact position on each side because if the distance from upper pole of breast to nipple is the same on each side, you will have the nipples positioned properly. The incision is closed with the Benelli suture. This suture has also been described by Dr. Robert Ersek. (Ersek, R. Circular cinching stitch. Plast. Reconstr. Surg. 88: 350, 19910. Prolene 4-0 running suture is used to close the areolar border/skin.

In our first four years of using this circumareolar technique for the reduction mammoplasties, reduction mastopexies, and mastopexies with augmentations, we did not use the circumareolar suture. Since 1990, we have used a single suture of 2-0 white Mersilene to form the purse-string suture. (See Stedman's Medical Dictionary 24th Ed. for definition of various types of sutures, including the purse-string suture.) We always leave the knot at the 6 o'clock position for easy location if necessary post operative. The remainder of the incision is closed with simple 5-0 Prolene running sutures and the patient is taped with Benzoin and steristrips. She is placed in a foam or elastic type bandage to help form the breast and keep it supported and she is put into a bra and told absolutely do not remove the bra in the erect position for any cause for at least three weeks.

After one or two weeks, we remove the elastic or supportive tape, or if the patient has an allergic reaction to the tape she is told to pull it back and trim it away from the reactive area or to remove the tape if necessary, but anything like this would be done with her in the reclining position. The bra is an underwire bra with nonelastic straps kept tight, day and night, for at least three weeks, including taking a shower in the bra; then she can lie down and change her bra. After the first three weeks she can take a shower without the bra on, but she still must wear the bra day and night for another three weeks.

What we accomplish here is akin to fixation of a broken bone which can be plated and then cast, but if the cast were removed every day just to allow for bathing of the extremity, the plate cannot hold properly. Here, once the sutures are put in place, the breast has been restored to its normal position, but if it is going to heal there it has to be held in position for a sufficient period of time. FIG. 8 shows the preop status of the breast 1, while FIG. 8A shows the repaired breast 1, both in section.

CIRCUMAREOLAR MASTOPEXY WITHOUT AUGMENTATION

To perform a either a simple mastopexy (breast elevation) or a reduction mammoplasty, the determination must be made as to what volume of breast will remain after the surgery and subsequent postoperative atrophy, in order to determine if that volume will make the patient the size she would like to have. The amount of postoperative atrophy can be the most significant factor between having a happy patient or unhappy patient.

Post operative atrophy has been discussed in the literature by Balch (Balch, C. The central mound technique for reduction mammoplasty. Plast. Reconstr. Surg. 67: 305, 19810 and Boyola (Boyola, A. Breast reduction with short L. scar. Plast. Reconstr. Surg. 85: 728, 1990) and is also discussed below in connection with the endoscopic augmentation mammoplasty.

If the patient's primary request is for a mastopexy, the procedure is to first determine what is the patient's breast volume. In the ptotic breast (FIG. 8) the most simple method to estimate volume is usually with the patient wearing a good fitting bra. Before planning a mastopexy the determination must be made if the patient is happy with the volume she has with her bra on, and would she be unhappy if her breasts were ⅓ to ½ cup smaller after surgery. If she can accept this volume loss, the mastopexy can be done with a good result and a happy patient. If she cannot accept the volume loss, she needs a mastopexy with volume addition.

With the mastopexies we determine during the preoperative office visit the estimated final long term postoperative breast volume, taking into account the fact there will be a twenty to twenty five percent loss of volume in the long term post operative phase. Our estimate assumes the patient will undergo no significant weight gain or loss.

The mastopexy patient's breast 1 is also marked in pre-anesthesia (FIGS. 2a & 2b) for the appropriate location of the nipple 11 in the midclavicular line about eighteen to twenty centimeters from the suprasternal notch, depending on the patient's height. Any difference in nipple distances would be noted here and this would be compensated for as previously explained in the mastopexy with augmentation.

The patient is then placed under general endotracheal anesthesia, prepped and draped in the standard manner, given IV antibiotics, and the breasts 1 marked for the margins. The nipple 11 is marked for the approximate size depending upon what the patient wants or what would be idea for her size. If there is excessive areolar border, it is also marked for excision with a concentric circle type incision 10a. The size of the outside circle being only as large as necessary to remove whatever excessive areolar border may be there, but at least large enough to gain the appropriate length of incision for exposure.

Figure 5:
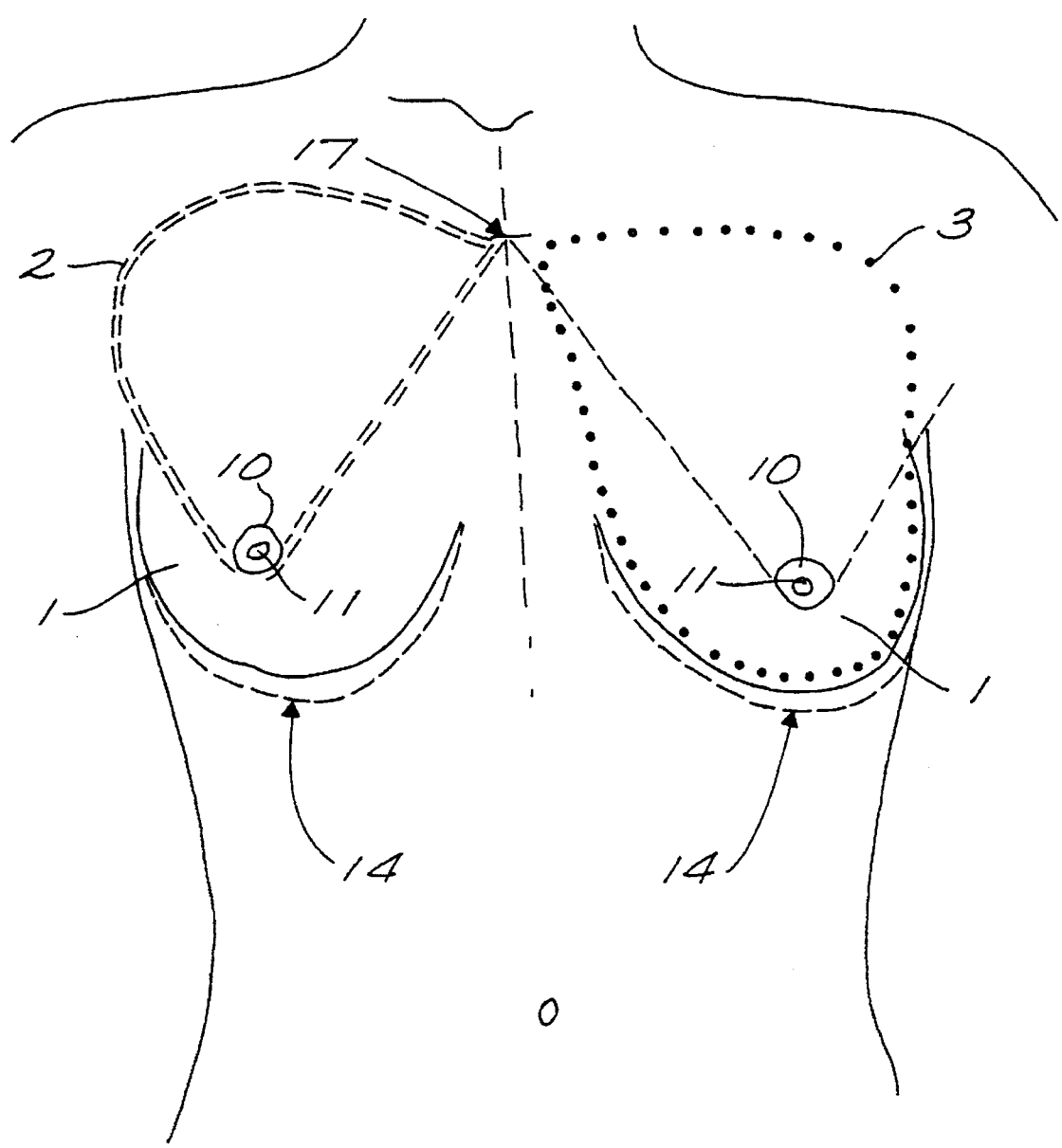
FIG. 5 shows the boundaries of undermining the skin in the reduction mammoplasty and the mastopexy with and without prosthetic augmentation.

The additional markings which are made on the reduction mastopexy versus the mastopexy with augmentation is a line marked around the lower hemisphere of the breast, staying about two centimeters up on the breast away from the chest wall and then as the line comes to about the 9 o'clock position it advances toward the axilla, and from the 3 o'clock it advances toward the sternal angle, see FIG. 5.

Figure 9:
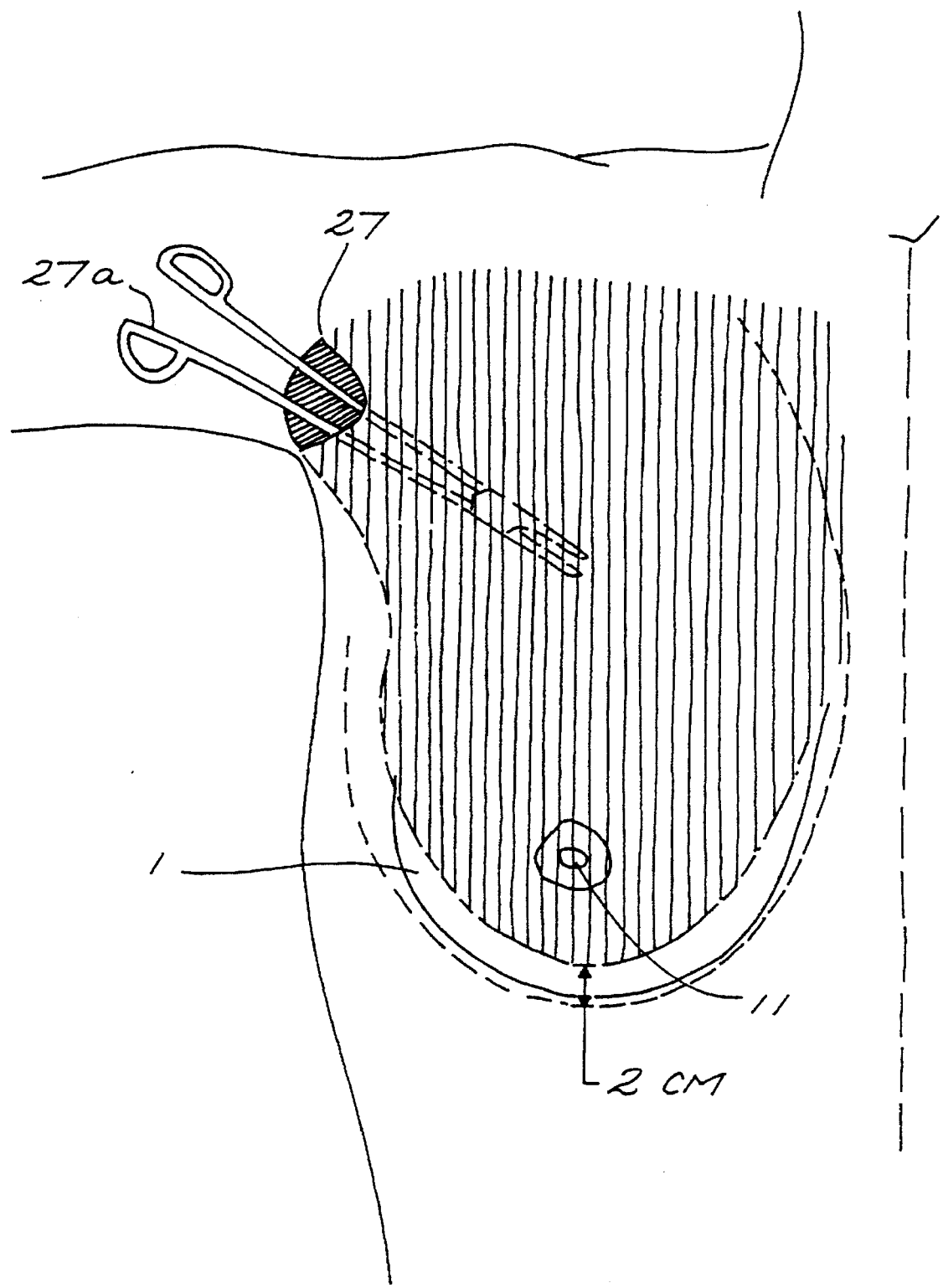
FIG. 9 shows undermining the skin from fascia and breast tissue, but excluding the nipple, in the reduction mastopexy.

A stab wound 18 is made in the lower portion of the areolar border and the subcutaneous tissue is infiltrated with a solution the same as used for liposuction for the tumescent technique and as described in the mastopexy with augmentation. The infiltration is accomplished over the entire surface of the breast down to the chest wall including the part of the unmarked 2 cm margin of skin. (FIGS. 6 & 9)

The incision is then made and de-epithelialization done as previously described. Sharp dissection with scissors is used for all dissection that involves undermining to create a thin skin flap. When the upper pole of the breast is reached, the electrocautery is used to carry the dissection down through the soft tissue to the fascia of the muscle.

The dissection is continued over the fascia above the second rib and to within about one centimeter of the clavicle, and as described in the mastopexy with augmentation, the upper pole of the breast is then freed away from the fascia only down to the level between the 3 and 9 o'clock position. This results in the upper hemisphere of the breast being completely detached.

Figure 10:
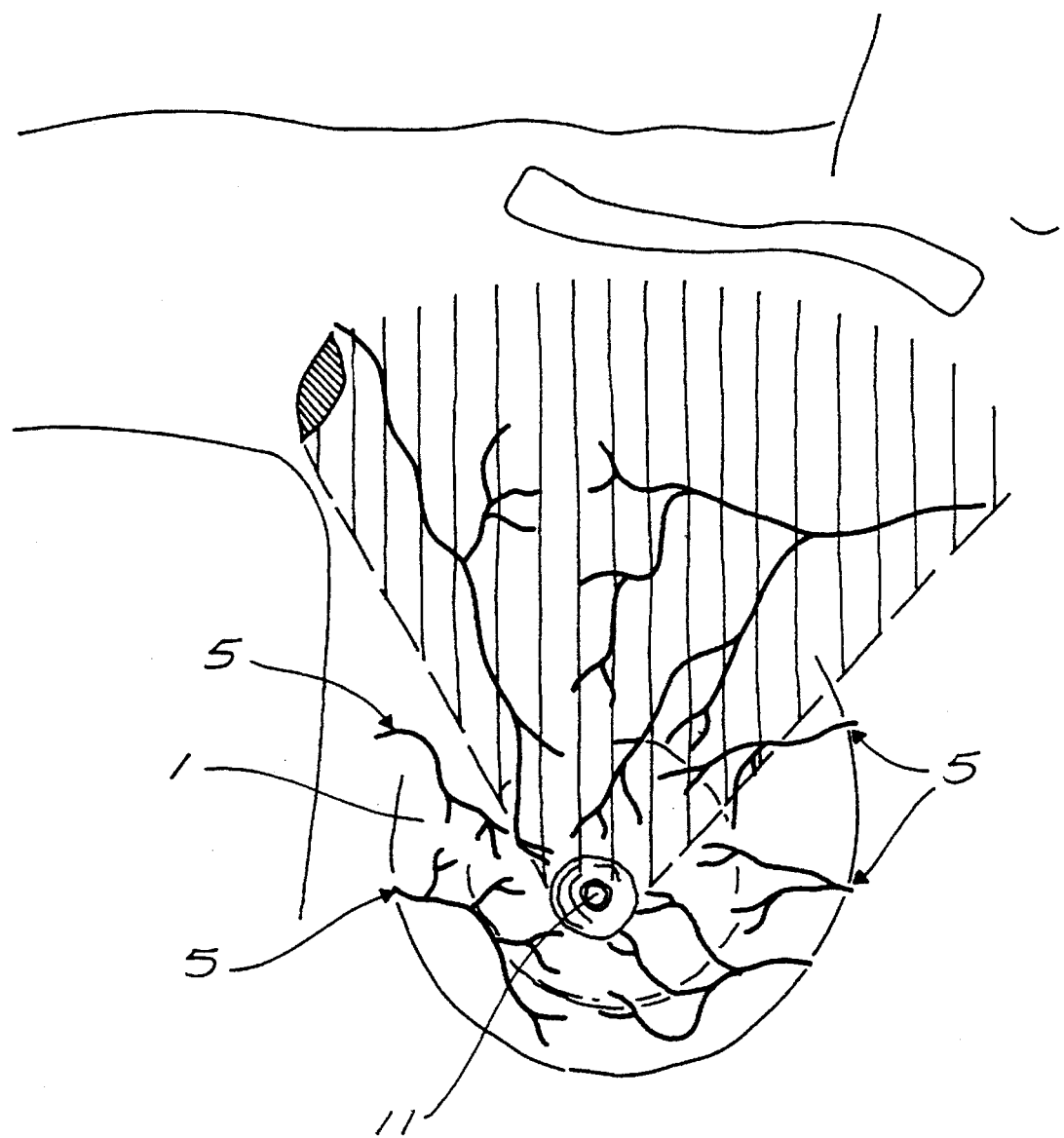
FIGS. 10 and 10a are views in elevation and in section, respectively, showing the blood supply in a breast undergoing surgery.
Figure 10A:
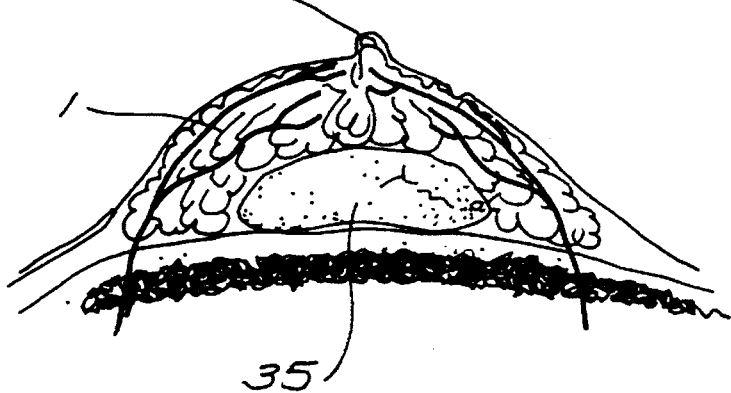
Figure 11:
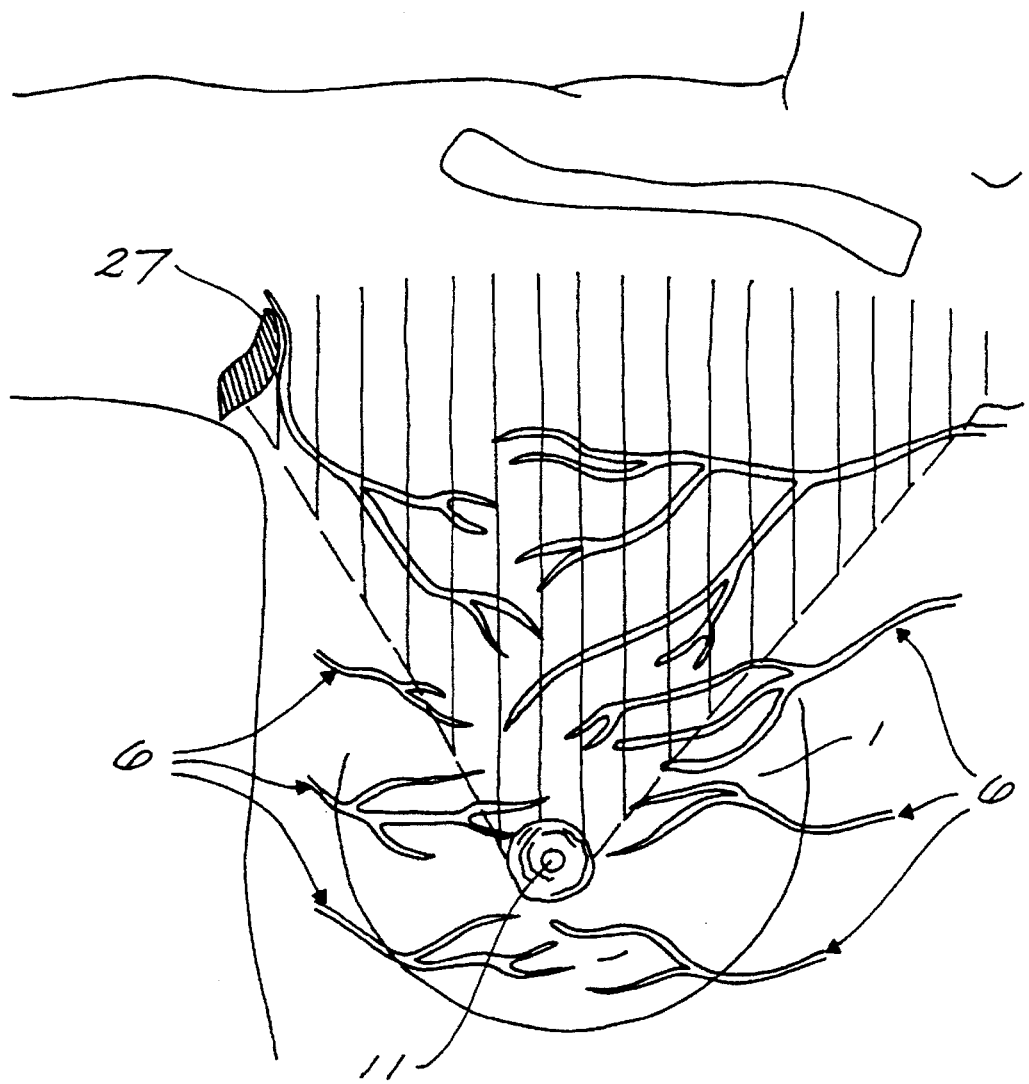
FIGS. 11 and 11a are views in elevation and in section, respectively, showing the nerve supply in a breast undergoing surgery.
Figure 11A:
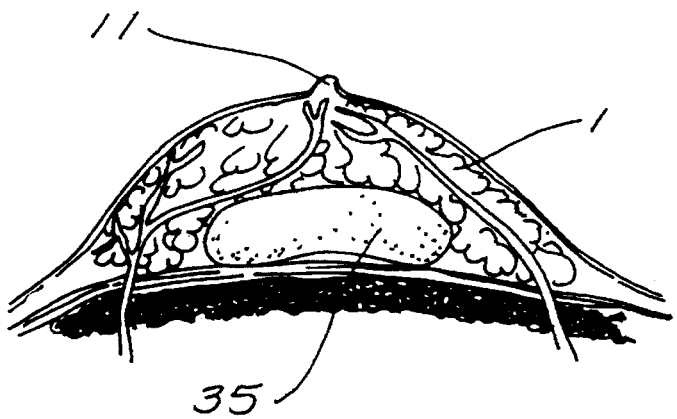
Figure 12:
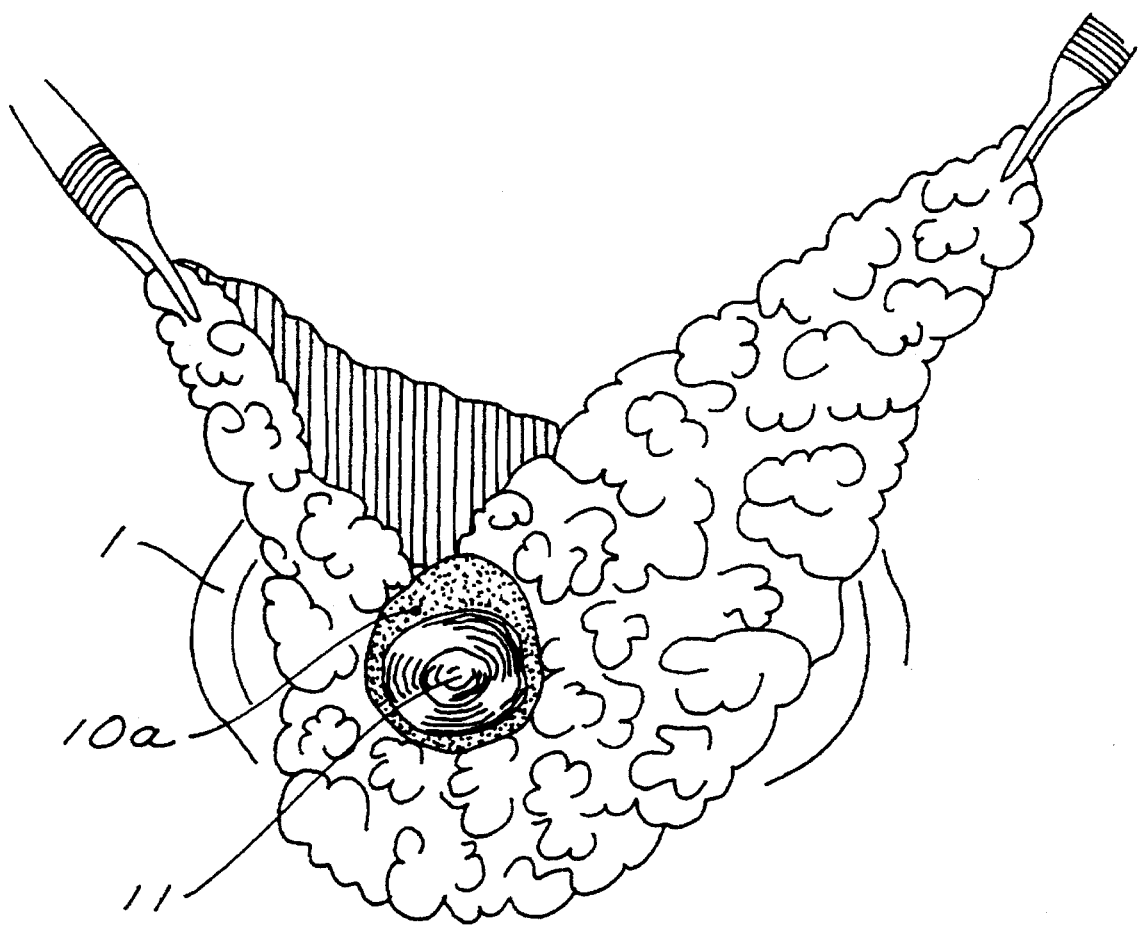
FIG. 12 shows the upper hemisphere of the breast divided into two flaps (two quadrants), upper medial and upper lateral in surgery.

The lower hemisphere of the breast is not detached from the fascia and the viability and sensation are preserved via the important medial and lateral blood 5 (FIG. 10) and nerve 6 (FIG. 11) supply to the breast and nipple through the gland and 2 cm pedicle of skin that is not detached. (FIGS. 10 & 11) From about the 12 o'clock position, or the "north pole of the upper hemisphere," an incision is made straight through the breast tissue from anterior to posterior surface to within about 1 to 2 cm of a line vertical to the nipple. The upper hemisphere of the breast has now been divided into two flaps (2 quadrants), upper medial and upper lateral. (FIG. 12)

Figure 13:
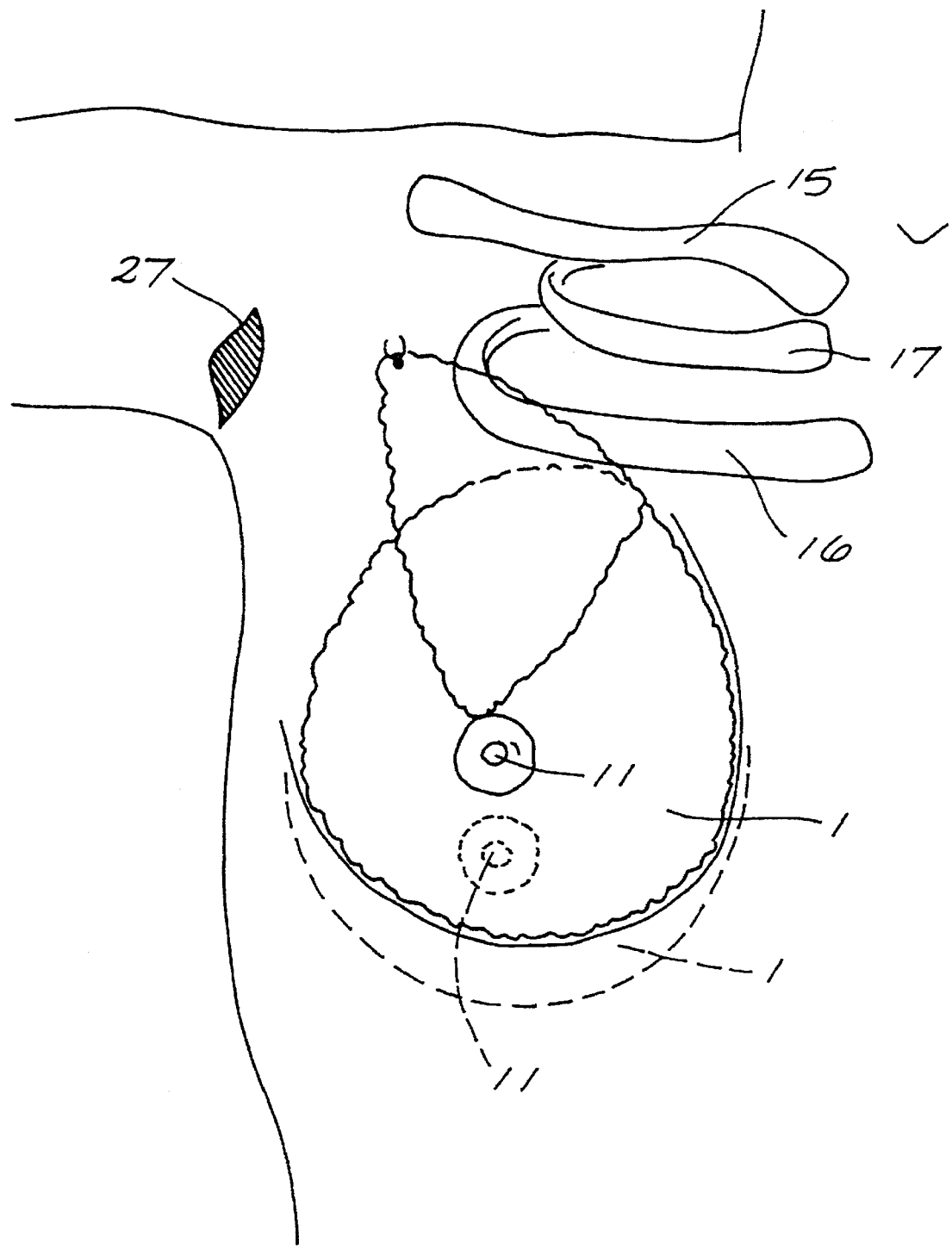
FIG. 13 shows a conization of the breast, increased projection, and elevation of the breast and nipple by the upper quadrant being picked up at the 12 o'clock position and this lateral quadrant is advanced up and medially and sutured to the surgically exposed fascia and muscle above the second rib and near the clavicle.

To effect a conization of the breast, increase projection, and elevation of the breast and nipple, the upper quadrant is picked up at the 12 o'clock position and this lateral quadrant is advanced up and medially and sutured to the surgically exposed fascia and muscle above the second rib and near the clavicle. (FIG. 13) The point of attachment which is secured with 2-0 Vicryl or Dexon. The lateral margin of that upper outer quadrant flap is sutured in two or three more places to help secure it to its new position on the chest wall.

Figure 14:
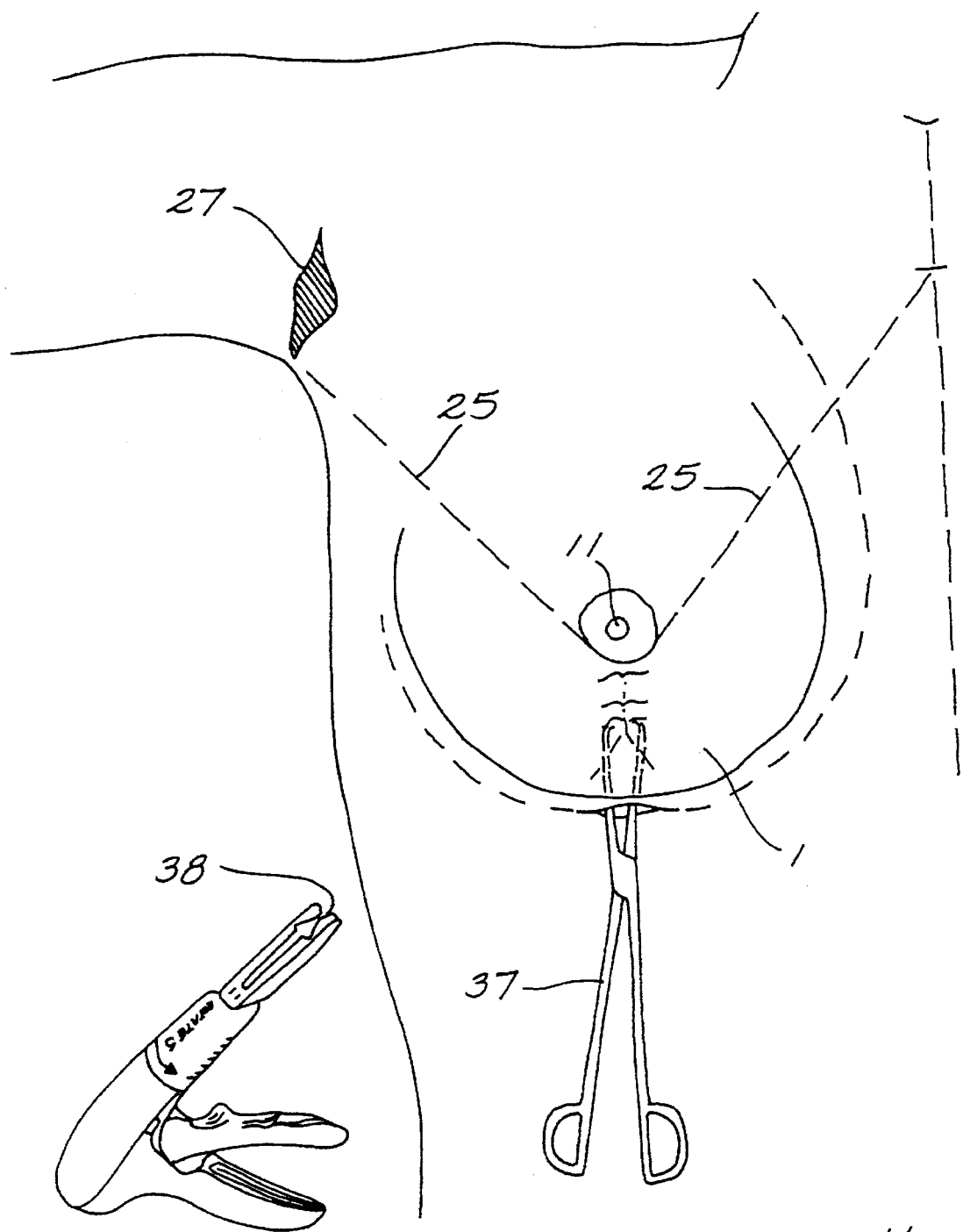
FIG. 14 shows the use of fascial staples and tenaculum in plication of the breast.
Figure 14A:
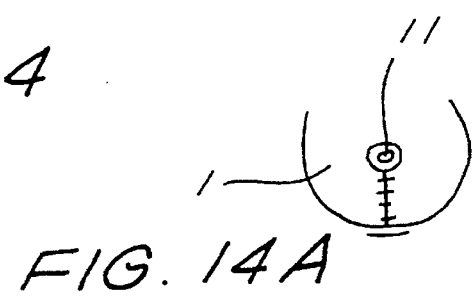
FIG. 14a shows a detail of the plication.

The upper inner quadrant flap is picked up at the 12 o'clock position and advanced up and lateral toward the roll of the pectoral muscle. This overlapping of quadrants results in an elevation and conization of the breasts. Most often some additional treatment is needed on the lower hemisphere because it remains "flat." Treat the lower hemisphere like plication of the rectus muscles a little more release of the 2 cm skin margin in the inframammary crease midline, then imagine a line from the areolar to 6 o'clock in the inframammary area. Invaginate that line from nipple to crease and suture over it to tighten and cone the lower hemisphere of the breast. With the exposure available through a circumareolar incision, we normally use the 2-0 suture. However, with the endoscopic approach we find it convenient to use fascial staples. (FIG. 14).

Sometimes there may be too much fatty tissue in the lower portion to provide adequate strength and tension for the plication, and what we do if necessary is take the liposuction with a flat (or single port) suction tip and suction the fat off the breast enough to expose fibrous tissue that can be sutured to plicate the breast. The pocket is irrigated well and in these cases we seldom, if ever, drain these breasts. If there is any fluid collection postoperative, we simply tap it off with a needle. The incision is closed, dressings and supportive tape and a bra or compressive bandage applied in these patients the same as described in the mastopexy with agumentation procedure. Post operative instructions are also the same.

REDUCTION MAMMOPLASTY

The reduction mammoplasty (FIGS. 2c & 2d), through the circumareolar incision, is technically more difficult than simply doing the mastopexy, but is not so difficult as for the average plastic surgeon not to be able to do the procedure. The real problem can occur where a very large breast that is going to require 1,000 or 1,500 gram reduction from each breast and the nipple incision is found too small.

Making a larger concentric circle incision will allow more area for manipulation. The reduction mammoplasty patient is marked preop and prepped and draped in the same manner as a matopexy patient. One minor difference is in preanesthesia we are more likely to make a few extra marks to do some adjunctive suction on a large lateral breast roll or excessive axillary fat pad. Other markings in surgery are made the same as described on the mastopexy, and the saline/xylocaine infiltration is done in the same manner. The incisions and dissection are the same also, up to and including the 12 o'clock to nipple division of the surgically freed upper hemisphere.

The determination must have been made in the preoperative evaluation of how much, or at least an approximation of how much, volume or weight would be removed form each breast. The lateral quadrant of the upper hemisphere is picked up at the 12 o'clock point and advanced into or toward the sternal angle. With application of the amount of pull (force) the surgeon feels is reasonable, an estimate is made of the volume/weight of the breast tissue ion the upper lateral flap that is being displaced (pulled) across a line from the midclavicular position to the nipple (0° north line). The same determination is made with the upper inner quadrant.

Figure 15:
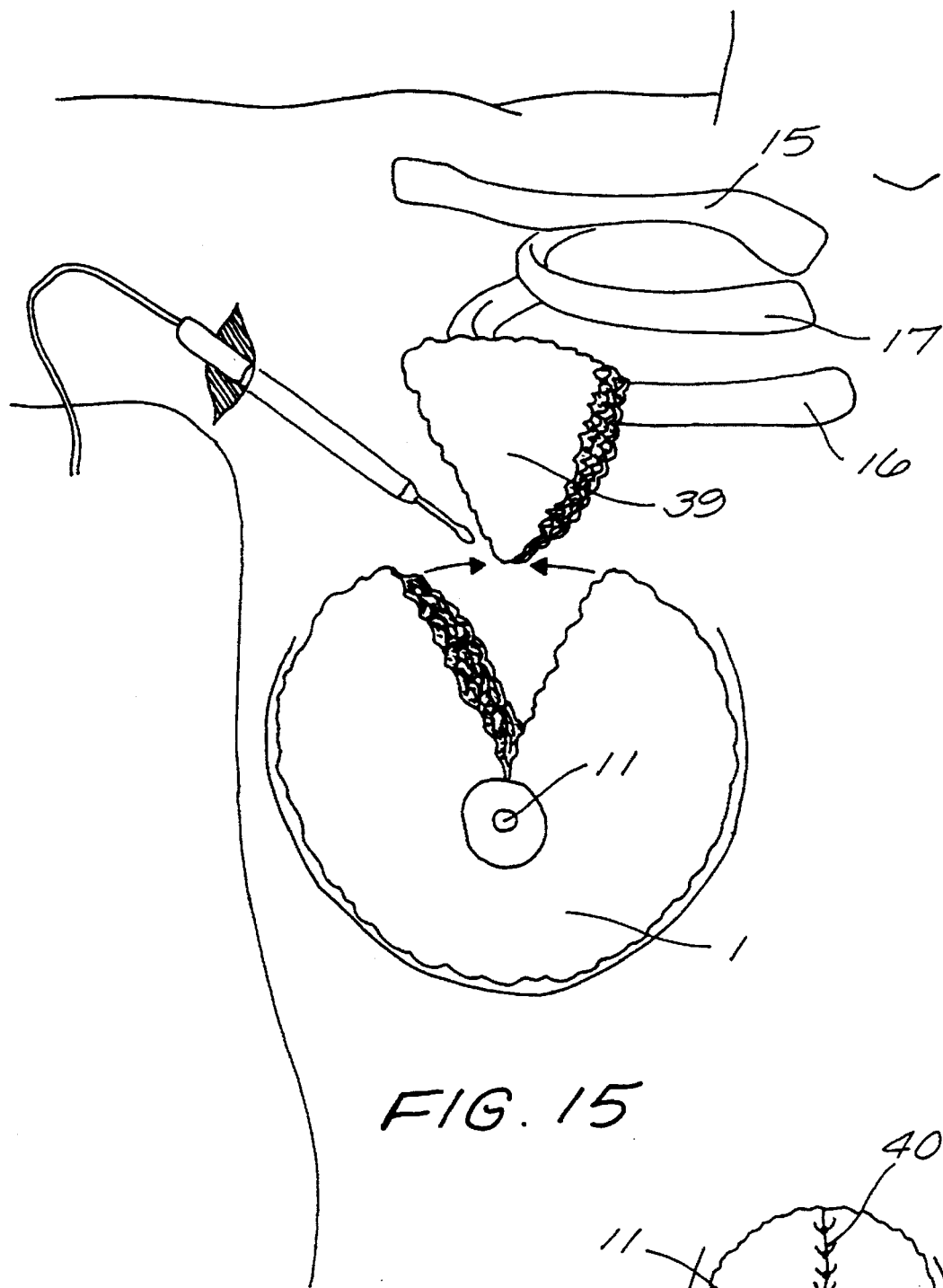
FIG. 15 shows removal of a wedge of breast tissue, followed by suturing the edges together, in a reduction mastopexy.
Figure 15A:
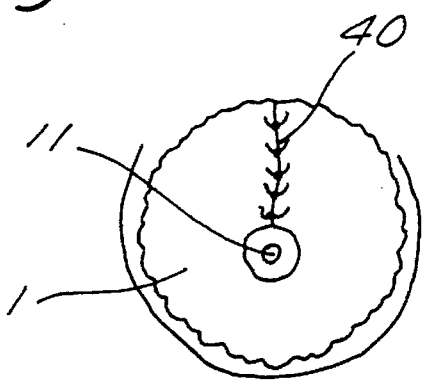
FIG. 15a shows a detail of the suturing.
Figure 16:
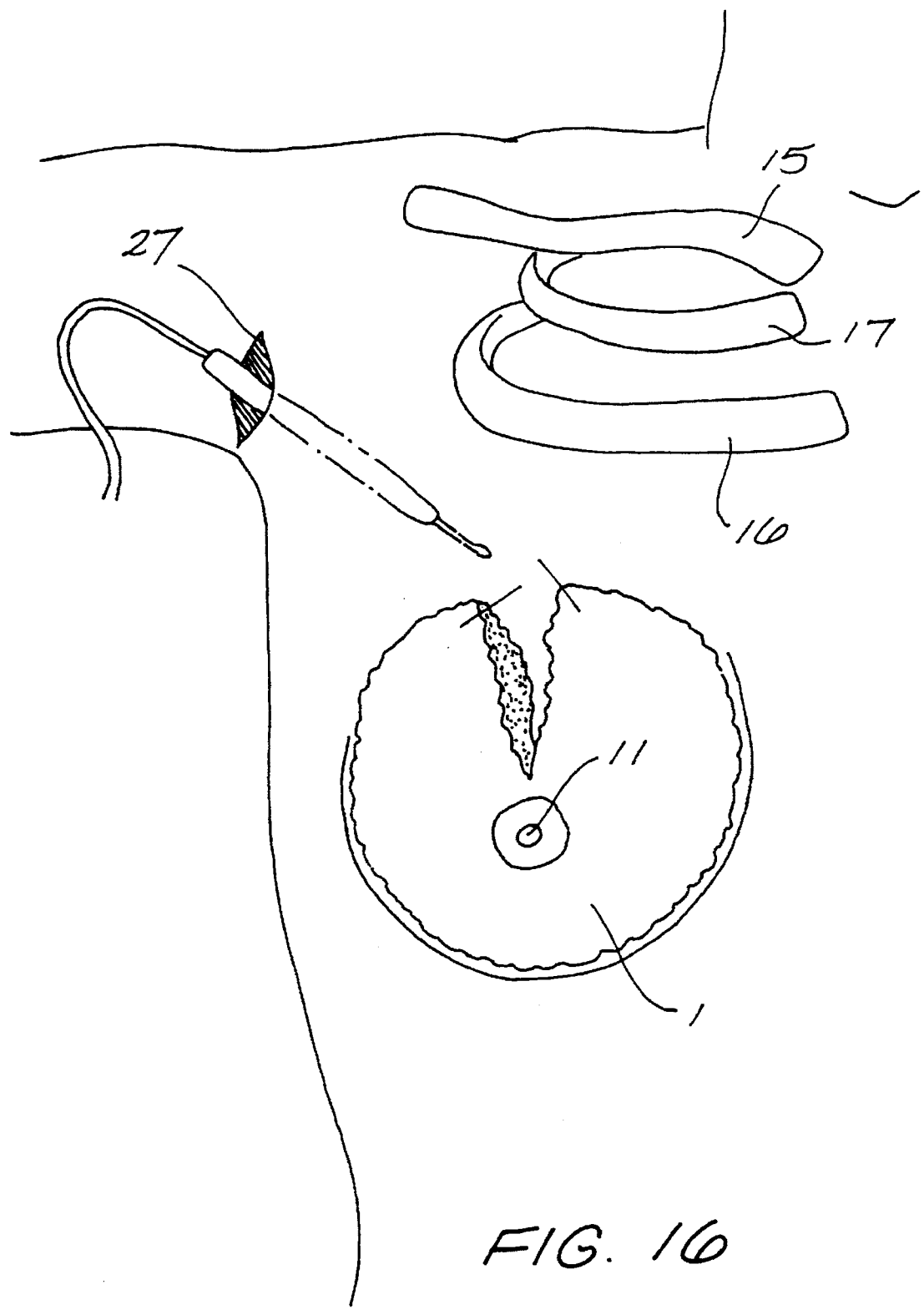
FIG. 16 shows dividing the breast tissue, followed by elevating the breast by suturing the lateral portion first and the overlapping medial portion second.

If the intraoperative estimate of volume or weight as described in this paragraph is equal to or greater than the volume removal the surgeon estimated pre operative, proceed to excise the appropriate amount of tissue from each quadrant. (FIG. 15, 16) If the intraoperative estimate of volume is less than the preoperative estimate, a little more careful undermining of the lower hemisphere and extend the release of the medial and lateral attachments (to perhaps the 4 to 8 o'clock position). The adjustments of the lower hemisphere attachments should allow the surgeon to remove the proper volumes from both quadrants. There remains no excessive tissue that needs overlapping, therefore suture the "new" 12 o'clock positions of each upper quadrant to fascia/muscle above the second rib. Three to four 20 sutures should be used in each flap, and the two flaps should be sutured together. The lower hemisphere is handled the same way as described for the mastopexy and the skin closure and taping and dressings are likewise handled the same.

DESCRIPTION OF THE PREFERRED EMBODIMENTS

THE ENDOSCOPIC APPROACH

ENDOSCOPIC AXILLARY MASTOPEXY WITH AUGMENTATION

We have found that technically the endoscopic assisted mastopexy with augmentation is the most simple and generally produces very good results. Preoperative, anesthesia, prep and drape and intraoperative antibiotics are the same as in the circumareolar procedures. The most significant difference in the two techniques is the location of the arms during surgery. With the circumareolar technique the arms are on arm boards at a 90° angle. In the endoscopic axillary approach, an ether screen is used and the forearms and hands are secured horizontally, leaving good exposure of the axilla without undue stress on any nerves or joints.

Figure 17:
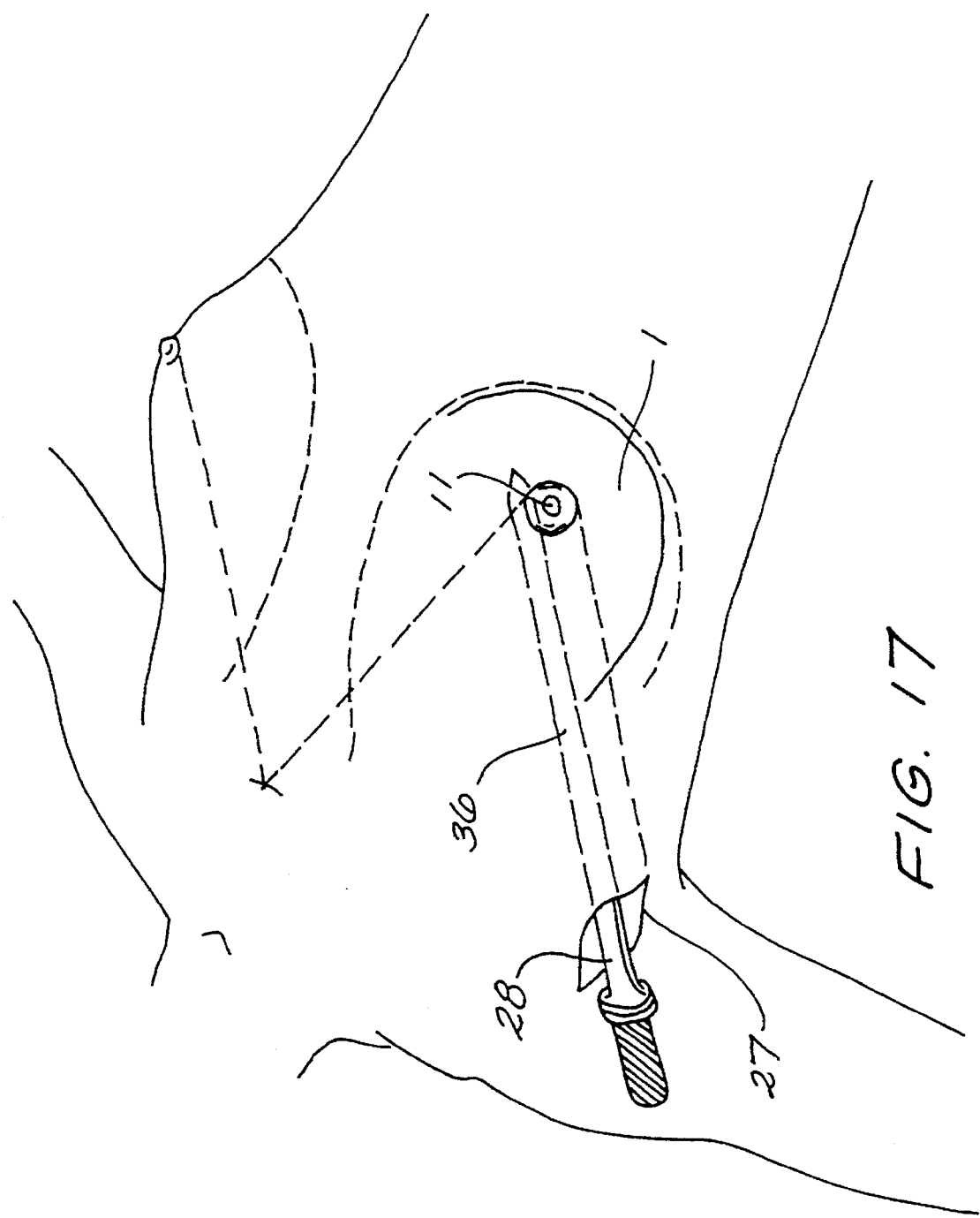
FIG. 17 shows insertion of the endotube from the axilla over the pectoral fascia.

The patient is then prepped and draped with both axilla exposed the pocket is designed, the 90° lines 25, 26 which go from the sternal angle to the nipple and from the nipple to the axilla which delineates the upper quadrant of the breast, these lines are marked and then the filtration is done. (FIG. 14) After the filtration has been done, the incision 26 is made in the axilla and the dissection is carried up to the fascia of the pectoralis muscle and getting above the fascia and with the scope for visualization, the endotube 28 is then inserted and passed from the axilla over the pectoral fascia (FIG. 17) in the same manner as if one were going to do an axillary subglandular augmentation.

Figure 19:
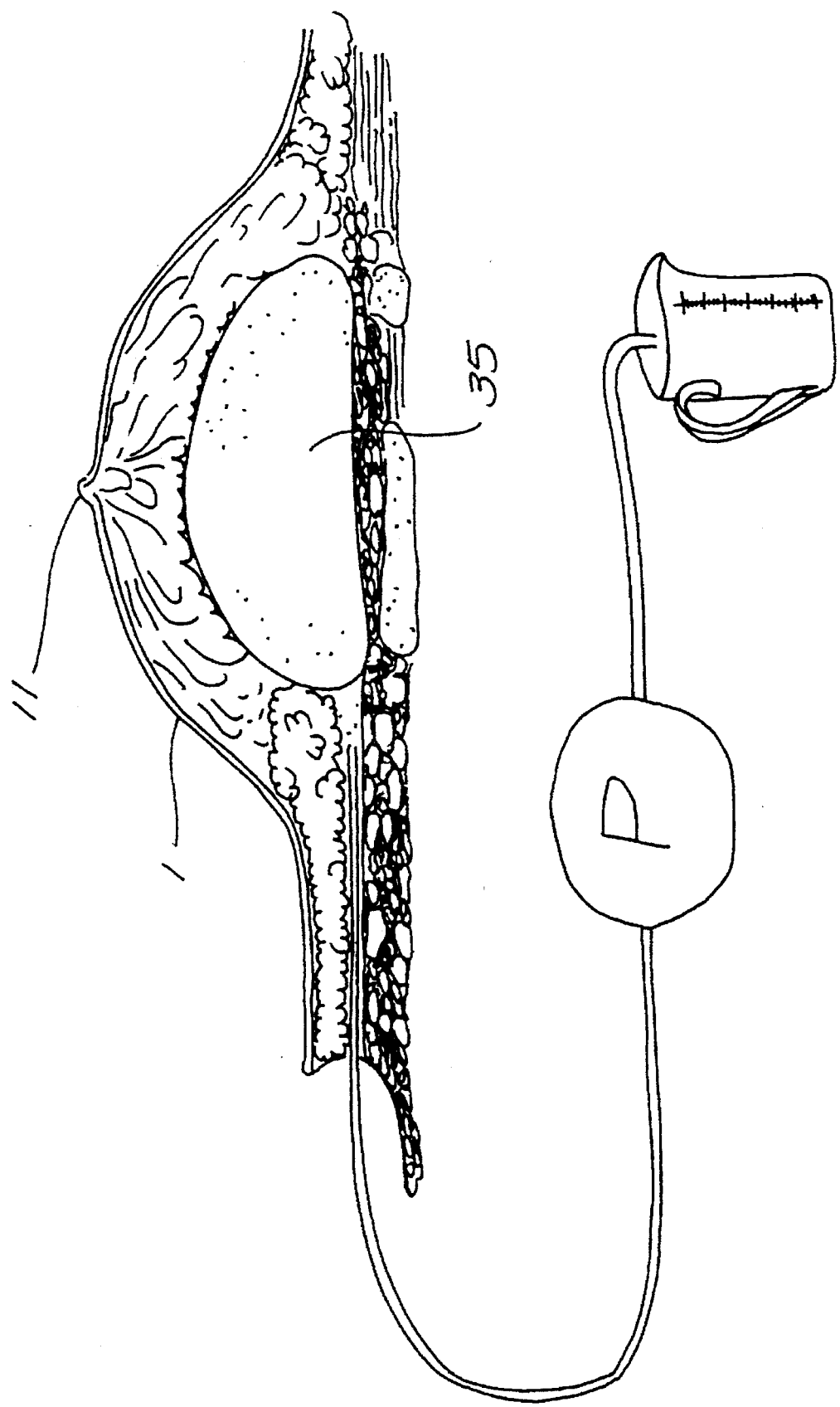
FIG. 19, in section, shows the filling of a tissue expander to form a pocket to receive an implant or prosthesis.

The tissue expander 29 is put in (FIG. 18) and is inflated over fifty percent of the size of the implant to be used. It causes no damage to inflate even more if you like, because what we are doing here is dissecting the posterior pocket 30. (FIG. 18 & 19) We are dissecting the fascial away from the muscle. The expander 29 is removed. At this point, with blind dissection, with external palpation, using the scissors, from the axilla, the undermining of the skin is accomplished in the upper quadrant. This undermining, once again, is the same as if it were being done from a circumareolar incision, except it is being approached from the axilla.

Figure 20:
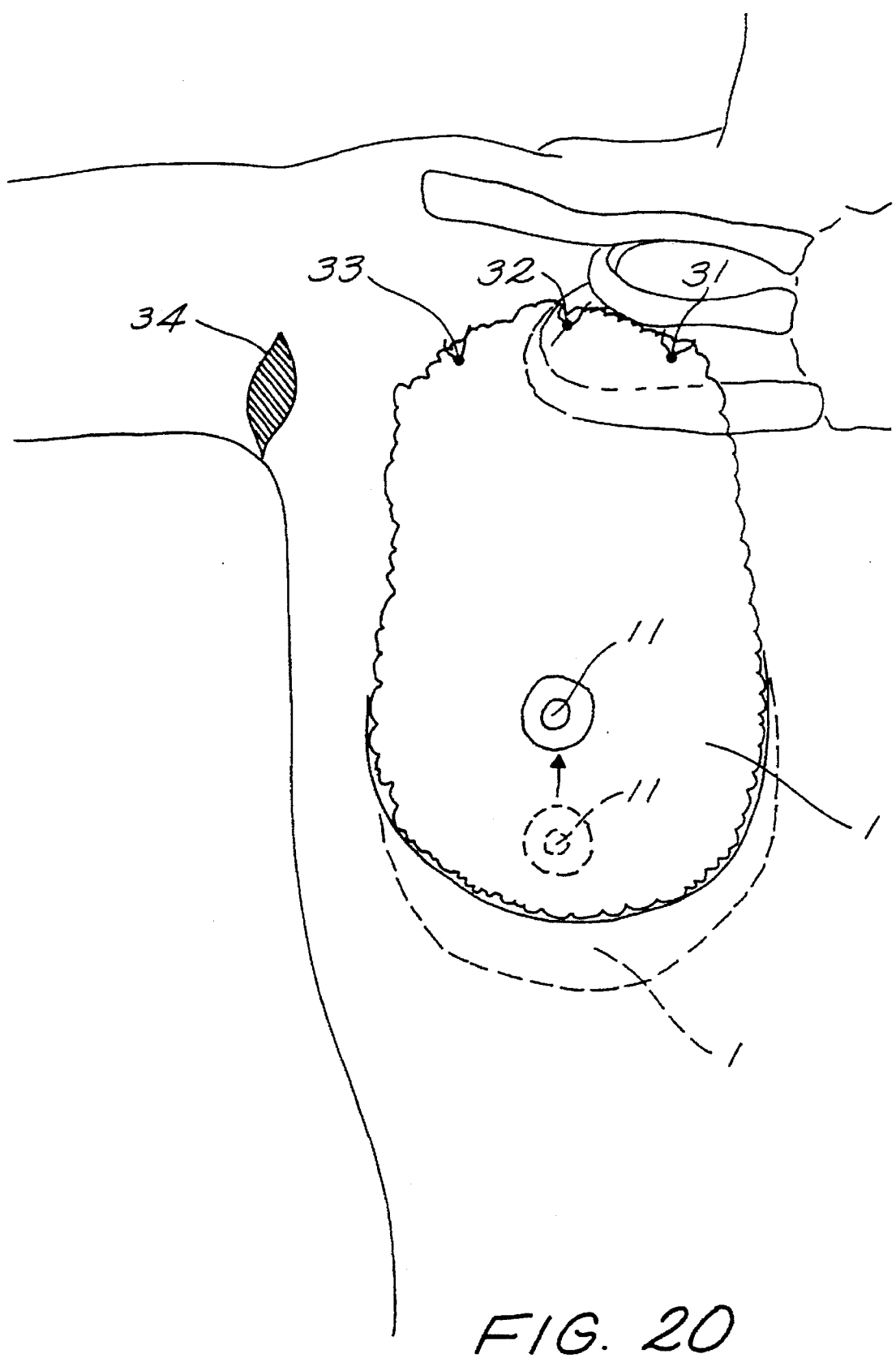
FIG. 20 shows the elevation of the breast by suturing the upper pole into the prepectoral fascia, with the suture again going through a portion of the breast, fascia and muscle.

Once the undermining has been done up to what we feel is the upper margin of the breast tissue, the pocket is then connected from the subcutaneous position. The breast tissue is then released by cutting the breast tissue loose so that there is now a direct communication from the subcutaneous pocket around to the postglandular pocket. This again is the same method that was used on the circumareolar, it is just a different approach. The dissection is continued now by elevating the soft tissue away from the pectoralis muscle and fascia going up above the second rib and just below the clavicle. At this point, with the upper breast having been released properly one can then grip the upper fold of the breast with the forceps 27a and pull upward and see how well it lifts the nipple areolar complex. In FIG. 20, the dotted lines indicate the position of the breast and nipple prior to surgery and the full lines indicate the position after surgery.

At this point, the upper pole of the breast is then sutured into the fascia, (FIG. 20) prepectoral fascia, with the suture again going through a substantial portion of the breast with the fascia and some to the muscle. Usually using at least three to four sutures of 2-0 Dexon or Vicryl, the first suture 31 being put in the medial most portion and then the second suture 32 and third 33 and fourth suture 34 finally out at the axillary area. Once this has been accomplished, then there is still an opening from the axilla into the subglandular space.

Figure 21:
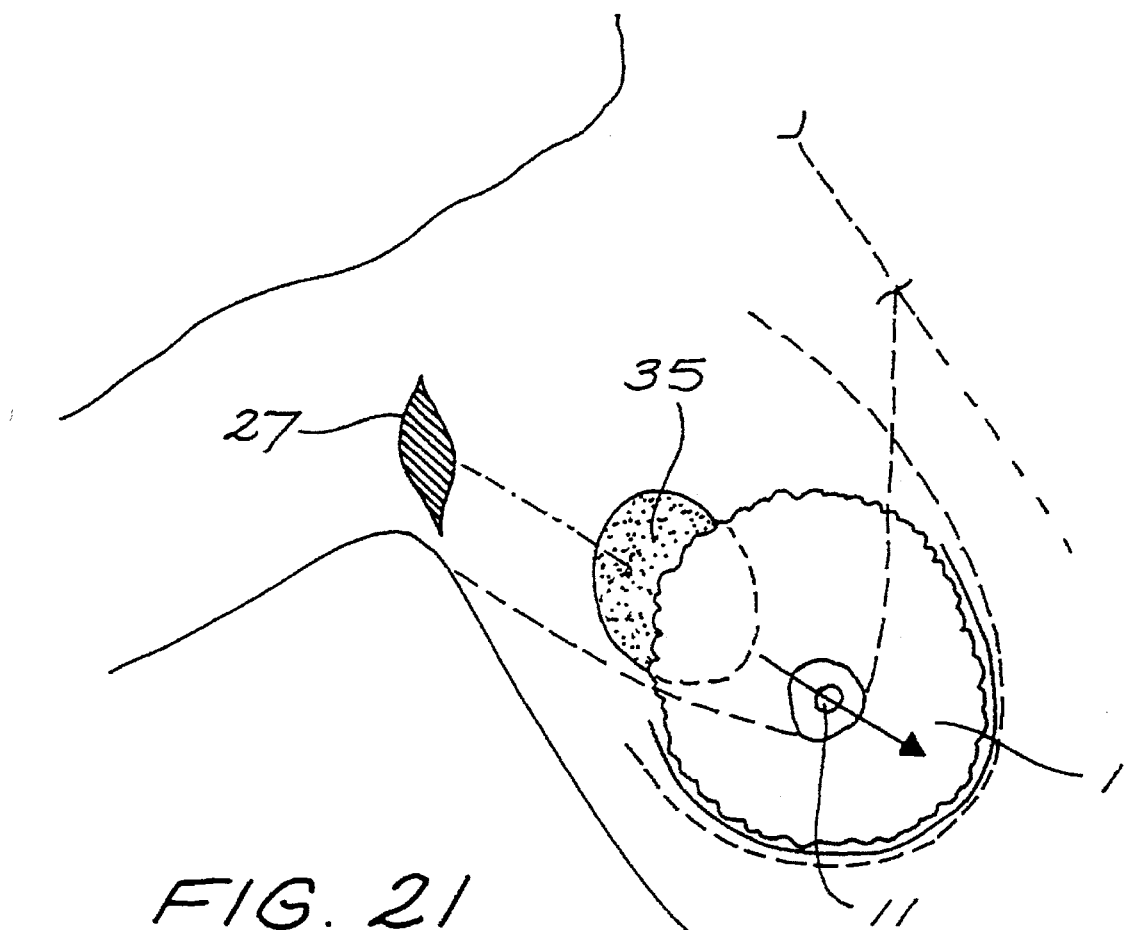
FIG. 21 shows an implant rolled up and placed into the pocket formed between the breast ad the pectoralis and inflated.
Figure 21A:
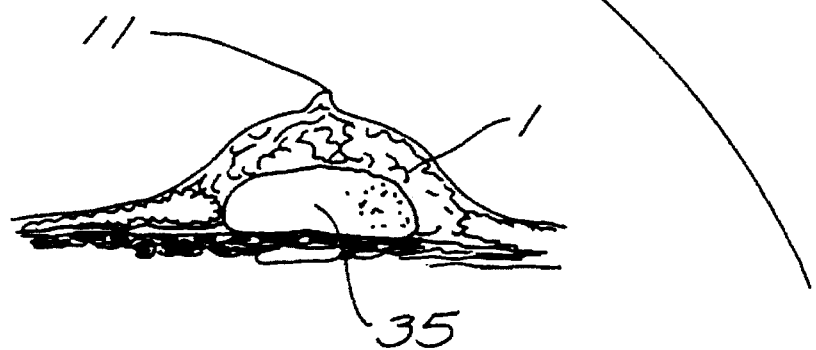
FIG. 21a in a section on FIG. 21 showing the inflated implant.

An implant 35 is rolled up and placed into this pocket (FIG. 21) and then inflated again in the same manner as if one were doing the endoscopic augmentation simply through an axillary approach. Once this has been completed, the incision 27 is closed with subcutaneous sutures of Dexon or Vicryl and reinforced with steristrips. The patient is dressed in the same way that the mastopexy with augmentation through a circumareolar incision would be dressed. The same kind of support is needed over the same period of time to allow this to heal properly.

THE ENDOSCOPIC MASTOPEXY WITHOUT AUGMENTATION

The next approach is the axillary endoscopic mastopexy without augmentation. This technique is approached in a similar fashion to the circumareolar mastopexy without augmentation with a few changes. First, there is no circumareolar incision, and second, there is an axillary incision 27. Thirdly, there is a possibility that the areolar border is too large in the person who needs a mastopexy, in which case, the areolar border is reduced in size by a purse-string suture that is placed through four stab wounds so that there is no incision made around the areolar border.

The procedure is begun by the patient being marked in pre-anesthesia. She is placed under general anesthesia, given IV antibiotics, arms are positioned on the ether screen, and the chest and breasts are marked. From the 3 o'clock position at the nipple to the sternal angle; from the 9 o'clock position at the nipple to the axilla, and a line around the lower hemisphere staying about two centimeters above the chest wall up on the breast.

Once these markings are made, the stab wound 18 is made in the areolar and the tumescent technique is used for infiltration of the subcutaneous areal all over the breast, including the lower hemisphere to help prevent any bleeding. After infiltration an incision is made about six to eight centimeters long and dissection is carried up to the pectoralis muscle and then, using the endotube, a tunnel 36 is made above the muscle with the endoscope 28 to verify position and location, and a tissue expander 29 is put into place. This tunnel 36 is made generally in the upper portion of the breast since it is not necessary to undermine the entire pocket (or the lower hemisphere) on the mastopexy.

Figure 22:
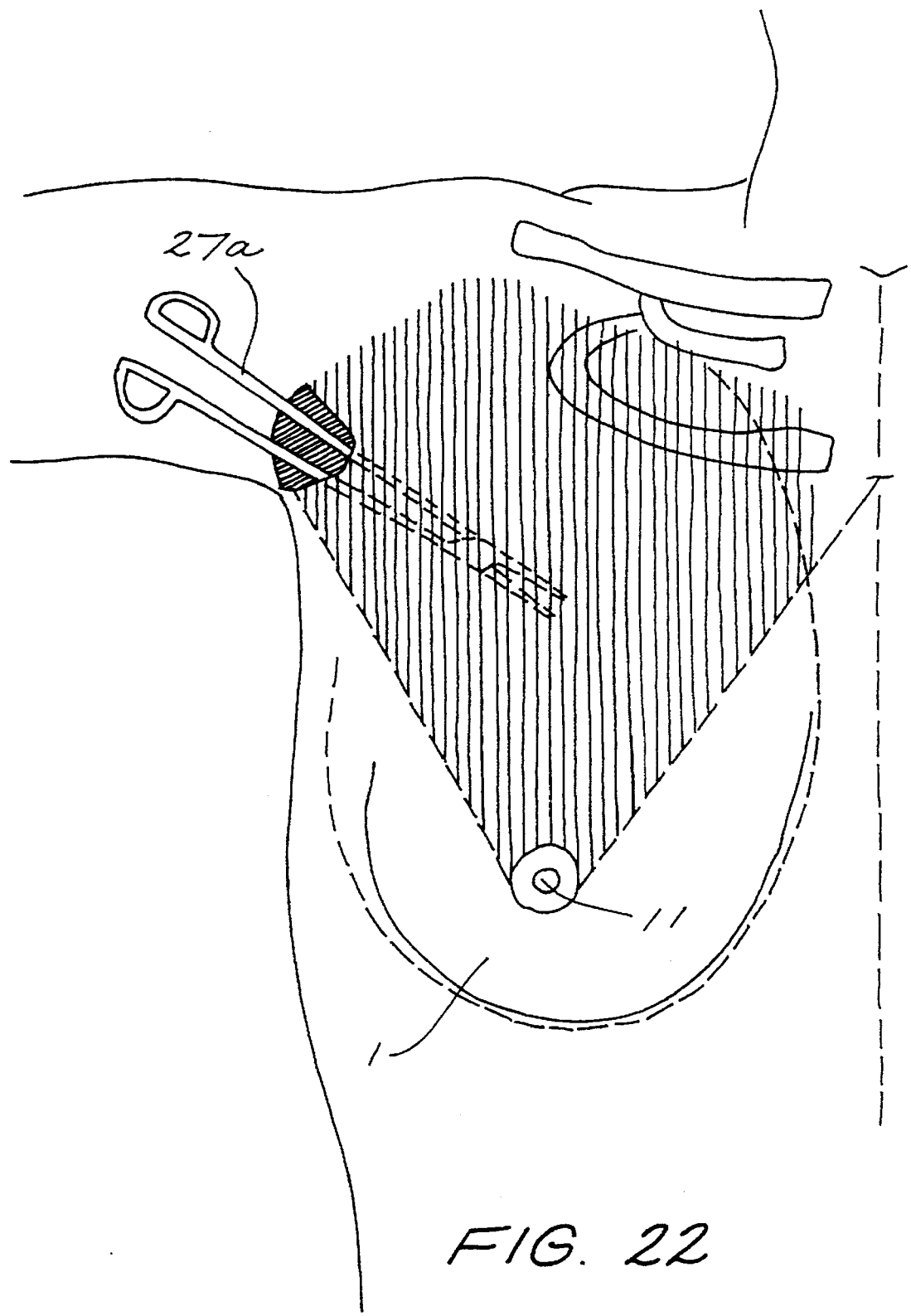
FIG. 22 shows the undermining over selected areas marked in order to free the skin from the glands.

The expander 29 is deflated and removed and subcutaneous undermining is done with sharp dissection (scissors) coming from the axilla 27 in a blind fashion palpating with one hand. The breast 1 is undermined over the entire portion of the areas marked in order to give complete freedom of the skin from the glands. (FIG. 22) If the areolar border needs to be made smaller, then the entire areolar will be undermined also. The nipple 11 is left intact and the ductal system is left intact. All the areolar border is undermined along with the rest of the skin.

After this has been accomplished, the subcutaneous pocket is then connected to the retromammary pocket in the upper portion of the breast by cutting through the soft tissue at this point and the dissection is continued up above the second rib to the clavicle. The upper hemisphere of the breast is divided through from of the 12 o'clock position to the nipple as we descried to the circumareolar reduction. This can be done either with the right angle pair of scissors or a very sharply curved pair of scissors done blindly, or under direct vision with the endoscope. If it is done blindly, the endoscope 28 may be needed to help control bleeding.

Once the upper hemisphere has been divided, the lateral flap is brought up and inward and sutured in place. The flap is then sutured in two or three additional places. The medial flap is brought up and outward and sutured in place with the medial part sutured first and the part to the lateral flap sutured and then the tip of the flap sutured over the muscle headed toward the axilla. The breast has now been elevated and coned to get projection as in the circumareolar mastopexy.

Next, attention is given to the lower portion of the breast. If the lower portion of the breast is fairly firm and does not really need anything done to it as far as projection, some minimal liposuction may be done superficially to help expose some fibrous tissue so that it can adhere back to the skin to help form a better shape and to help secure the breasts when bandaged. If, however, the breast is too flat and needs more projection, the 2 cm bridge of skin below the nipple is released down to the inframammary crease just below the nipple, and an incision is made about one and one-half to two centimeters long.

This incision will be below the area that has been undermined because we stayed two centimeters away. We then connect from the incision up to the undermined area and then, using the cervical tenaculum 37 and fascia stapler 38 as described above, the lower hemisphere is plicated to improve firmness and projection of the breasts. One more thing that may have to be done is if the patient's areolar border was too large or she wanted it to be smaller, then we make stab wounds; in addition to the one at 6 o'clock, at 3 o'clock, 9 o'clock, and 12 o'clock and then, using the circumareolar suture on a Keith needle or on a circular needle, we pass it around the nipple and use the purse-string suture to pull the nipple down to the appropriate size.

Since this entire areolar border has been undermined and a suture has pulled the nipple down to the proper size, when this patient is taped and put into a bra and kept in this bra for six weeks, she can expect that nipple will heal back to the tissue below in the proper position and in the proper size. She will have a nipple that is the proper size without having the circumareolar incision made around the nipple. The axillary incision is then closed with interrupted sutures of Dexon or Vicryl. She is dressed with a foam of elastic bandage to support the breast and placed and a bra and taken to the recovery room.

AXILLARY ENDOSCOPIC REDUCTION MAMMOPLASTY

In the axillary endoscopic reduction mammoplasty, the techniques are very similar to those described above for the axillary endoscopic mastopexy. The markings 3 (FIG. 5) are made from the 3 o'clock to the 9 o'clock position on the breast and two centimeters above the chest wall and then from the 3 o'clock position to the sternal angle and from the 9 o'clock position to the axilla. The stab wound 18 is then made in the infra-areolar area in the 6 o'clock position and the subcutaneous tissue over the entire breast is infiltrated with the tumescent technique to help control any bleeding.

The incision 27 is then made in the axilla. The approach is made to the pectoralis fascia and exposure of the fascia, allows the introduction of the endotube 28 and the endoscope into the pocket above the muscle and below the breast tissue, and the expander 29 is put into place. The expander 29 is expanded to create the retro mammary pocket.

The sharp dissection is then done blindly to dissect the skin and subcutaneous tissue free from the breast 1 over the entire breast surface and the areas that have been marked, including the areolar border, but excluding the nipple 11 and ductal system. When the undermining has been accomplished, the subcutaneous pocket is then connected superiorly to the retromammary pocket by dividing through the tissue to create the upper free flap of breast tissue, and then by dissecting around either blindly and then controlling bleeding with the scope or dissecting with the scope to the 3 o'clock position and then to the 9 o'clock position, whereupon the upper pole of the breast is free but the upper hemisphere is not free.

The dissection is carried on up over the pectoralis fascia up over the second rib up to just below the clavicle, and at this point then the division of the breast from the 12 o'clock position to the nipple is accomplished either under direct vision with electrocautery and the scope or done blindly with curved or sharp angled scissors. The upper hemisphere is thus formed into two flaps, the medial quadrant flap and the lateral quadrant flap. At this point, the amount of excessive tissue that can be ressected is removed from the medial flap and the amount that can be ressected is removed from the lateral flap.

An easier way to do this, is to estimate ahead of time how much wedge can be removed, how much needs to be removed in order to reduce to the volume you want to be, and then simply remove the wedge 39 of breast tissue (FIG. 15, 16) with the point of the wedge being toward the nipple and base of the wedge being in the periphery of the breast in the upper quadrant of the breast. Once this has been accomplished and bleeding controlled once again, the medial portion of the medial flap is sutured to the fascia above the second rib.

Additional sutures as necessary are put in that portion of the flap and then the most medial portion of the medial flap is sutured to the 12 o'clock position. The medial portion of the lateral flap is then sutured, at 40, to the 12 o'clock position. The remainder of the lateral flap is sutured around the lateral portion of the chest. Sutures are then put from the 12 o'clock position toward the nipple to suture the two flaps together.

At this point, the attention is then turned to the lower portion of the breast and the incision has already been made. Some suction is done as necessary to have enough fat removed so there is good fibrous breast tissue present. Then, using the tenaculum 37 and the staple gun 38, this is plicated in the inframammary portion of the breast. Once this is completed, the purse-string suture is place around the nipple starting at the 6 o'clock position going around the nipple using the Keith needle or curved needle and tightening this down. Once again, with the areolar border being undermined, and the patient taped and held this way, this will heal without having to make an incision around the nipple. The axillary incision is closed with subcutaneous sutures of Dexon or Vicryl.

After the closure of the axillary area, the patient is then placed in the foam tape or the elastiplast and placed in a bra, and again this is a six week time period for recovery.

LONG TERM RESULTS

Long term results have been very good. We have had in one case some skin loss on both breasts in a major reduction where we reduced around 1,500 cc's volume from each side with axillary technique. But even with some skin loss on each side, there was no loss of sensation in the nipple. The patient has basically normal sensation in both nipples, so this technique has a lot of merit. But the long term results we think we can correlate the axillary surgery to the circumareolar since both internal techniques are the same, but with the circumareolar we have eight years experience with this, having started this in 1986. We have done sufficient procedures through this endoscopic technique to consider it successful.

These procedures include reduction mammoplasties, reduction mastopexies, and mastopexies with augmentation. We feel that long term results are excellent and there is certainly not the tendency for descent of the breast nor for bottoming out of the breast that are seen in the inferior pedicle technique. This is also a technique that recognizes all five of the primary goals of the patient and the surgeon. And those goals, to recapitulate, are:

1. A breast of ideal size for the patient elevated to normal position on the chest wall.

2. A breast of ideal form or shape for the patient.

3. A breast with a minimal amount of scarring or visible scarring.

4. A breast with normal sensation and erectile function of the nipple.

5. A breast that could lactate and function for nursing if required.

So, while the circumareolar technique comes close to fulfilling all these goals, the axillary technique, especially when it can be used without having to make an incision around the nipple to make the nipple smaller, can really come almost one hundred percent to fulfilling these goals.

While this invention has been described fully and completely, it should be understood that, within the scope of the appended claims, the invention may be practiced otherwise than as specifically described.

I claim:

1. A method of breast surgery of a human patient comprising the steps of making a first incision at a point on the body of said patient under the armpit, or in a preexisting scar, or other substantially unobservable location which is accessible to the upper hemisphere of the breast, inserting a surgical cutting instrument through said first incision and undermining the skin above the fascia over a selected area of the upper hemisphere of the breast to separate the skin from the underlying breast tissue which is to be altered surgically, surgically removing breast tissue or adjusting the position of breast tissue beneath the skin and above the fascia through said incision, and suturing or closing said first incision.

2. A surgical method according to claim 1 in which said first incision is made in a preexisting scar.

3. A surgical method according to claim 1 in which said first incision is made under an armpit.

4. A surgical method according to claim 3 comprising a mastopexy including marking the breasts of the patient with lines going from the nipple to the axilla and from the nipple to the sternal angle to define an area for undermining, using a long infiltration needle infiltrating the subcutaneous areas of the breast are infiltrated in an area from the nipple to the sternal angle and from the nipple to the mid-axillary area and up to the clavicle, making said first incision up to the pectoralis muscle, making a tunnel above the muscle with an endoscope in the upper portion of the breast to verify position and location, placing an inflatable tissue expander into said tunnel and expanding the same to form a pocket behind the upper hemisphere of the breast, deflating and removing said tissue expander, undermining a selected area to give complete freedom of the skin from the glands, continuing the dissection up above the second rib to the clavicle and the upper margin of breast tissue, surgically dividing the upper hemisphere of the breast through along a vertical line to the nipple, bringing the lateral flap up and inward and suturing it in several places, bringing the medial flap up and outward and suturing it in place with the medial part sutured first and the part to the lateral flap sutured and then the tip of the flap sutured over the muscle headed toward the axilla, thus elevating and coning the breast to produce a desired projection, and closing and suturing said first incision.

5. A surgical method according to claim 4 comprising a mastopexy including removing fat by liposuction to expose fibrous tissue prior to surgically dividing said breast.

6. A surgical method according to claim 4 comprising a mastopexy including releasing a 2 cm bridge of skin below the nipple down to the inframammary crease just below the nipple and making an incision about one and one-half to two centimeters long, and connecting from the incision up to said undermined area and then, using a cervical tenaculum plicating the lower hemisphere and suturing or stapling the same to improve firmness and projection of the breast.

7. A surgical method according to claim 6 comprising a mastopexy including surgically undermining the areolar border of the breast through said first incision, making a plurality of equally spaced stab wounds around the periphery of the areola, and suturing said stab wounds internally through said first incision with a circumareolar, purse-string suture and drawing said suture to reduce the nipple to a predetermined size without making a circumareolar incision.

8. A surgical method according to claim 3 comprising a mastopexy with breast augmentation including marking the breasts of the patient with lines going from the nipple to the axilla and from the nipple to the sternal angle to define an area for undermining, using a long infiltration needle infiltrating the subcutaneous areas of the breast from the nipple to the sternal angle and from the nipple to the mid-axillary area and up to the clavicle, making said first incision up to the pectoralis muscle, making a tunnel above the muscle with an endoscope in the upper portion of the breast to verify position and location, placing an inflatable tissue expander into said tunnel and expanding the same to dissect the fascia away from muscle to form a posterior pocket behind the upper hemisphere of the breast, deflating and removing said tissue expander, undermining a selected area up to the upper margin of breast tissue to give complete freedom of the skin from the glands, inserting a surgical cutting instrument through said first incision and dissecting the breast from the underlying fascia, inserting a surgical instrument through said first incision and moving said breast to a selected elevated position, working through said first incision, securing an upper portion of the breast to the prepectoral fascia to maintain it in said selected elevated position, inserting a hollow implant through said first incision to a pocket behind said breast, inflating said hollow implant with saline solution to a selected size, surgically undermining the areolar border of the breast through said first incision, making a plurality of equally spaced stab wounds around the periphery of the areola, suturing said stab wounds internally through said first incision with a circumareolar, purse-string suture and drawing said suture to reduce the nipple to a predetermined size without making a circumareolar incision, and closing and suturing said first incision.

9. A surgical method according to claim 3 comprising a reduction mammoplasty including marking the breasts of the patient from a 90° to a 270° position and about 2 cm. above the chest wall and then from the 90° position to the sternal angle and from the 270° position to the axilla to define an area for undermining, making a stab wound at the 180° position and using a long infiltration needle infiltrating the subcutaneous areas over the entire breast throughout the undermined area, making said first incision up to the pectoralis muscle, making a tunnel above the muscle with an endoscope in the upper portion of the breast to verify position and location, placing an inflatable tissue expander into said tunnel and expanding the same to form a pocket behind the upper hemisphere of the breast.

deflating and removing said tissue expander, undermining a selected area to give complete freedom of the skin from the glands, releasing a 2 cm bridge of skin below the nipple down to the inframammary crease just below the nipple and making an incision about one and one-half to two centimeters long, connecting from the incision up to said undermined area and then, using a cervical tenaculum plicating the lower hemisphere and suturing or stapling the same to improve firmness and projection of the breast, continuing the dissection up above the second rib to the clavicle and the upper margin of the breast tissue, surgically removing a wedge of breast tissue from the upper hemisphere of the breast to produce two flaps, bringing the lateral flap up and inward and suturing it in several places, bringing the medial flap up and outward and suturing it in place with the medial part sutured first and the part to the lateral flap sutured and then the tip of the flap sutured over the muscle headed toward the axilla, thus elevating and coning the breast to produce a desired projection, p1 releasing a 2 cm bridge of skin below the nipple down to the inframammary crease just below the nipple and making an incision about one and one-half to two centimeters long, surgically undermining the areolar border of the breast through said first incision, making a plurality of equally spaced stab wounds around the periphery of the areola, and suturing said stab wounds internally through said first incision with a circumareolar, purse-string suture and drawing said suture to reduce the nipple to a predetermined size without making a circumareolar incision, and closing and suturing said first incision.

10. A surgical method according to claim 9 comprising a reduction mammoplasty including removing fat by liposuction to expose fibrous tissue prior to surgically dividing said breast.

11. A surgical method according to claim 1 including repeating each of the recited steps on a second breast.

12. A surgical method according to claim 1 including surgically undermining the areolar border of the breast through said first incision, making a plurality of equally spaced stab wounds around the periphery of the areola, and suturing said stab wounds internally through said first incision with a circumareolar, purse-string suture and drawing said suture to reduce the nipple to a predetermined size without making a circumareolar incision.

13. A surgical method according to claim 1 comprising a mastopexy including inserting a surgical cutting instrument through said first incision and dissecting the breast from the underlying fascia, inserting a surgical instrument through said first incision and moving said breast to a selected elevated position, and working through said first incision, securing an upper portion of the breast to the prepectoral fascia to maintain it in said selected elevated position.

14. A surgical method according to claim 1 comprising a mastopexy including
    making said first incision up to the pectoralis muscle,
    making a tunnel above the muscle with an endoscope in the upper portion of the breast to verify position and location,
    placing an inflatable tissue expander into said tunnel and expanding the same to form a pocket behind the upper hemisphere of the breast,
    deflating and removing said tissue expander,
    undermining a selected area to give complete freedom of the skin from the glands,
    continuing the dissection up above the second rib to the clavicle,
    surgically dividing the upper hemisphere of the breast through along a vertical line to the nipple,
    bringing the lateral flap up and inward and suturing it in several places,
    bringing the medial flap up and outward and suturing it in place with the medial part sutured first and the part to the lateral flap sutured and then the tip of the flap sutured over the muscle headed toward the axilla, thus elevating and coning the breast to produce a desired projection.

15. A surgical method according to claim 14 comprising a mastopexy including
    removing fat by liposuction to expose fibrous tissue prior to surgically dividing said breast.

16. A surgical method according to claim 14 comprising a mastopexy including
    releasing a 2 cm bridge of skin below the nipple down to the inframammary crease just below the nipple and making an incision about one and one-half to two centimeters long, and
    connecting from the incision up to said undermined area and then, using a cervical tenaculum plicating the lower hemisphere and suturing or stapling the same to improve firmness and projection of the breast.

17. A surgical method according to claim 16 comprising a mastopexy including
    surgically undermining the areolar border of the breast through said first incision,
    making a plurality of equally spaced stab wounds around the periphery of the areola, and
    suturing said stab wounds internally through said first incision with a circumareolar, purse-string suture and drawing said suture to reduce the nipple to a predetermined size without making a circumareolar incision.

18. A surgical method according to claim 1 comprising a mastopexy with breast augmentation including
    making said first incision up to the pectoralis muscle,
    making a tunnel above the muscle with an endoscope in the upper portion of the breast to verify position and location,
    placing an inflatable tissue expander into said tunnel and expanding the same to dissect the fascia away from muscle to form a posterior pocket behind the upper hemisphere of the breast,
    deflating and removing said tissue expander,
    undermining a selected area up to the upper margin of breast tissue to give complete freedom of the skin from the glands,
    inserting a surgical cutting instrument through said first incision and dissecting the breast from the underlying fascia,
    inserting a surgical instrument through said first incision and moving said breast to a selected elevated position,
    working through said first incision, securing an upper portion of the breast to the prepectoral fascia to maintain it in said selected elevated position,
    inserting a hollow implant through said first incision to a pocket behind said breast,
    inflating said hollow implant with saline solution to a selected size, and
    closing and suturing said first incision.

19. A surgical method according to claim 1 comprising a reduction mammoplasty including
    marking the breasts of the patient from a 90° to a 270° position and about 2 cm. above the chest wall and then from the 90° position to the sternal angle and from the 270° position to the axilla to define an area for undermining,
    making a stab wound at the 180° position and using a long infiltration needle infiltrating the subcutaneous areas over the entire breast throughout the undermined area,
    making said first incision up to the pectoralis muscle,
    making a tunnel above the muscle with an endoscope in the upper portion of the breast to verify position and location,
    placing an inflatable tissue expander into said tunnel and expanding the same to form a pocket behind the upper hemisphere of the breast,
    deflating and removing said tissue expander,
    undermining a selected area to give complete freedom of the skin from the glands,
    continuing the dissection up above the second rib to the clavicle and the upper margin of breast tissue,
    surgically dividing the upper hemisphere of the breast through along a vertical line to the nipple,
    bringing the lateral flap up and inward and suturing it in several places,
    bringing the medial flap up and outward and suturing it in place with the medial part sutured first and the part to the lateral flap sutured and then the tip of the flap sutured over the muscle headed toward the axilla, thus elevating and coning the breast to produce a desired projection, and
    closing and suturing said first incision.

20. A surgical method according to claim 19 comprising a reduction mammoplasty including
    removing fat by liposuction to expose fibrous tissue prior to surgically dividing said breast.

21. A surgical method according to claim 20 comprising a reduction mammoplasty including
    releasing a 2 cm bridge of skin below the nipple down to the inframammary crease just below the nipple and making an incision about one and one-half to two centimeters long, and
    connecting from the incision up to said undermined area and then, using a cervical tenaculum plicating the lower hemisphere and suturing or stapling the same to improve firmness and projection of the breast.

22. A surgical method according to claim 19 including
    cutting a selected amount of tissue from one of said flaps prior to suturing.

23. A surgical method according to claim 19 comprising a reduction mammoplasty including releasing a 2 cm bridge of skin below the nipple down to the inframammary crease just below the nipple and making an incision about one and one-half to two centimeters long, connecting from the incision up to said undermined area and then, using a cervical tenaculum plicating the lower hemisphere and suturing or stapling the same to improve firmness and projection of the breast, surgically undermining the areolar border of the breast through said first incision, making a plurality of equally spaced stab wounds around the periphery of the areola, and suturing said stab wounds internally through said first incision with a circumareolar, purse-string suture and drawing said suture to reduce the nipple to a predetermined size without making a circumareolar incision.

24. A surgical method according to claim 1 comprising a reduction mammoplasty including marking the breasts of the patient from a 90° to a 270° position and about 2 cm. above the chest wall and then from the 90° position to the sternal angle and from the 270° position to the axilla to define an area for undermining, making a stab wound at the 180° position and using a long infiltration needle infiltrating the subcutaneous areas over the entire breast throughout the undermined area, making said first incision up to the pectoralis muscle, making a tunnel above the muscle with an endoscope in the upper portion of the breast to verify position and location, placing an inflatable tissue expander into said tunnel and expanding the same to form a pocket behind the upper hemisphere of the breast, deflating and removing said tissue expander, undermining a selected area to give complete freedom of the skin from the glands, continuing the dissection up above the second rib to the clavicle and the upper margin of breast tissue, surgically removing a wedge of breast tissue from the upper hemisphere of the breast to produce two flaps, bringing the lateral flap up and inward and suturing it in several places, bringing the medial flap up and outward and suturing it in place with the medial part sutured first and the part to the lateral flap sutured and then the tip of the flap sutured over the muscle headed toward the axilla, thus elevating and coning the breast to produce a desired projection, and closing and suturing said first incision.

* * * * *